(12) United States Patent  
Nudler et al.

(10) Patent No.: US 7,511,076 B2
(45) Date of Patent: Mar. 31, 2009

(54) NITROSATION-INDUCIBLE INHIBITORS BIOLOGICAL MACROMOLECULES

(75) Inventors: Evgeny Nudler, New York, NY (US); Andrei Nedospasov, Moscow (RU)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/186,301

(22) Filed: Jul. 1, 2002
(Under 37 CFR 1.47)

(65) Prior Publication Data
US 2003/0087805 A1    May 8, 2003

Related U.S. Application Data

(63) Continuation of application No. 09/988,397, filed on Nov. 19, 2001, now abandoned.

(60) Provisional application No. 60/249,277, filed on Nov. 17, 2000.

(51) Int. Cl.
*C07C 307/02* (2006.01)
*A61K 31/18* (2006.01)

(52) U.S. Cl. .................................. 514/603; 564/86

(58) Field of Classification Search ................ 540/604; 546/205, 206; 514/217.12, 319, 603; 564/86
See application file for complete search history.

(56) References Cited

U.S. PATENT DOCUMENTS 5,399,487 A * 3/1995 Butenas et al. ................ 435/13

FOREIGN PATENT DOCUMENTS

LT        3910 B   *   4/1996
RU      1807986    *   4/1993

OTHER PUBLICATIONS

Butenas et al., CAPLUS Abstract 126:317661, 1997.*
Rodina et al., CAPLUS Abstract 122:75200, 1995.*
Butenas et al., CAPLUS Abstract 122:133843, 1995.*
Butenas et al., CAPLUS Abstract 124:317881, 1996.*

* cited by examiner

*Primary Examiner*—Deepak Rao
(74) *Attorney, Agent, or Firm*—Browdy and Neimark, PLLC

(57) ABSTRACT

Biomacromolecules such as proteins are inactivated by hydrophobic ANSA derivatives of the formula:

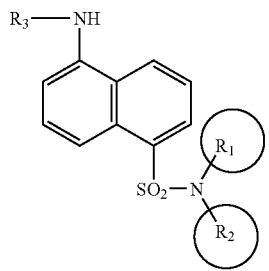

wherein $R_1$ and $R_2$ are hydrophobic or affinity groups and $R_3$ is selected from the group consisting of aminoacyl groups and peptidyl groups upon nitrosation. ANSA derivatives can be designed to selectively kill tumor cells and various pathogens, including bacteria, viruses, and fungi.

3 Claims, 17 Drawing Sheets

$$2 \cdot NO + O_2 \longrightarrow 2 \cdot NO_2$$

$$\cdot NO_2 \cdot NO \longleftrightarrow N_2O_3$$

$$(k = 6 \times 10^6 \, M^{-2} sec^{-2})$$

$$N_2O_3 + H_2O \longrightarrow NO^- \cdot NO_2^- + H_2O \longleftrightarrow 2HNO_2$$

ANSA                    peptidyl-ANSA

FIG.9
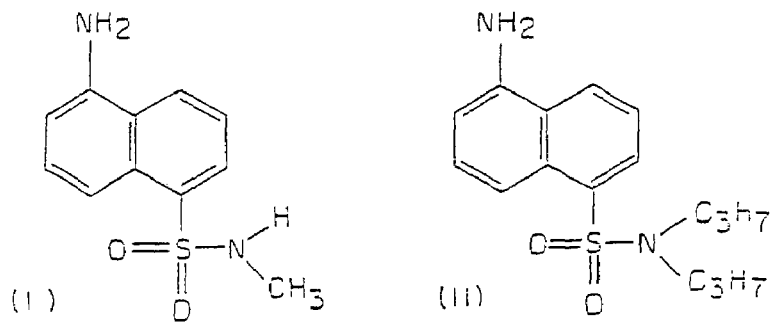
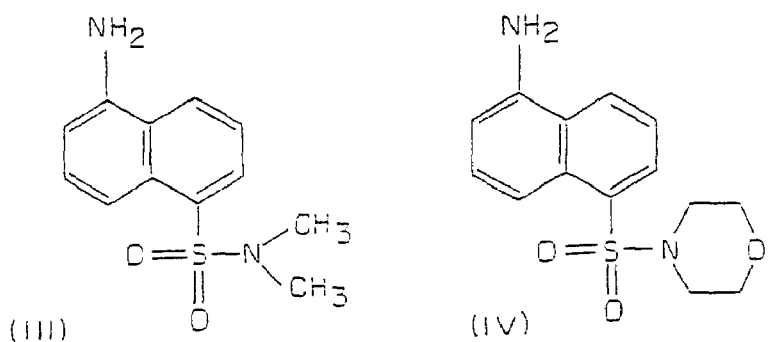
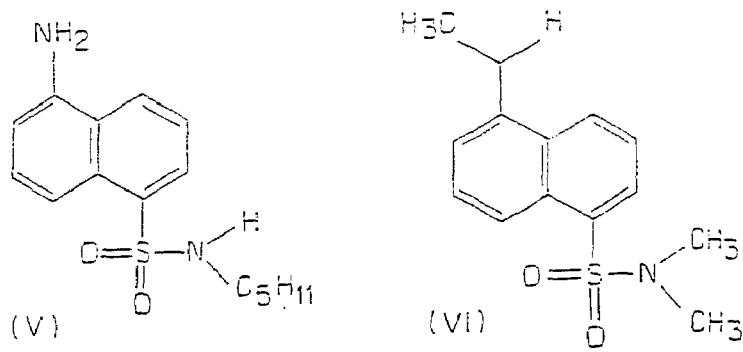
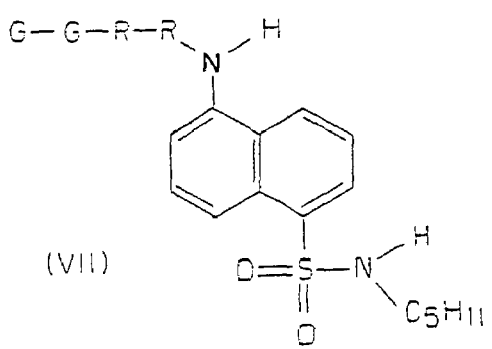

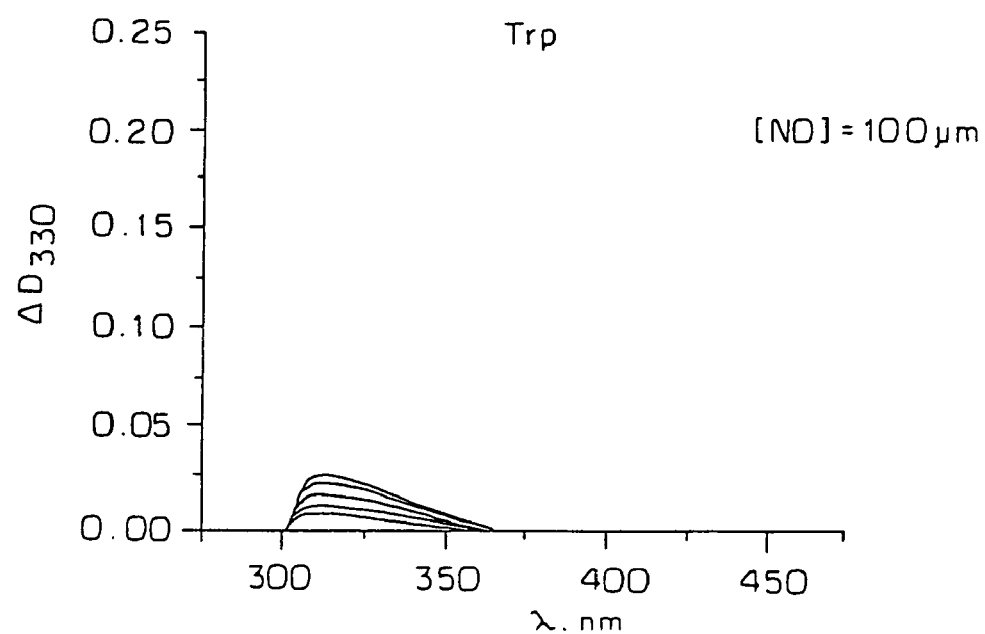

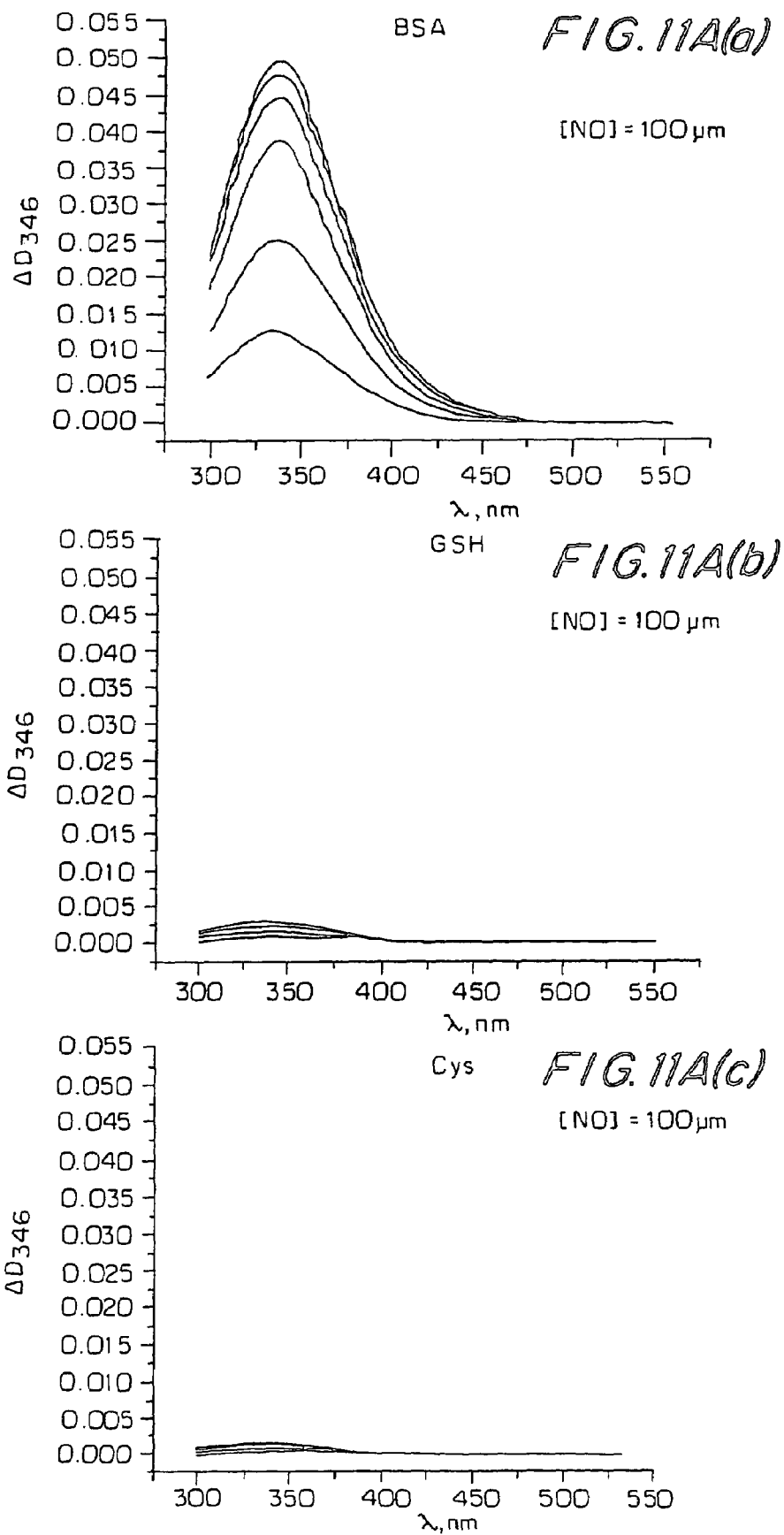

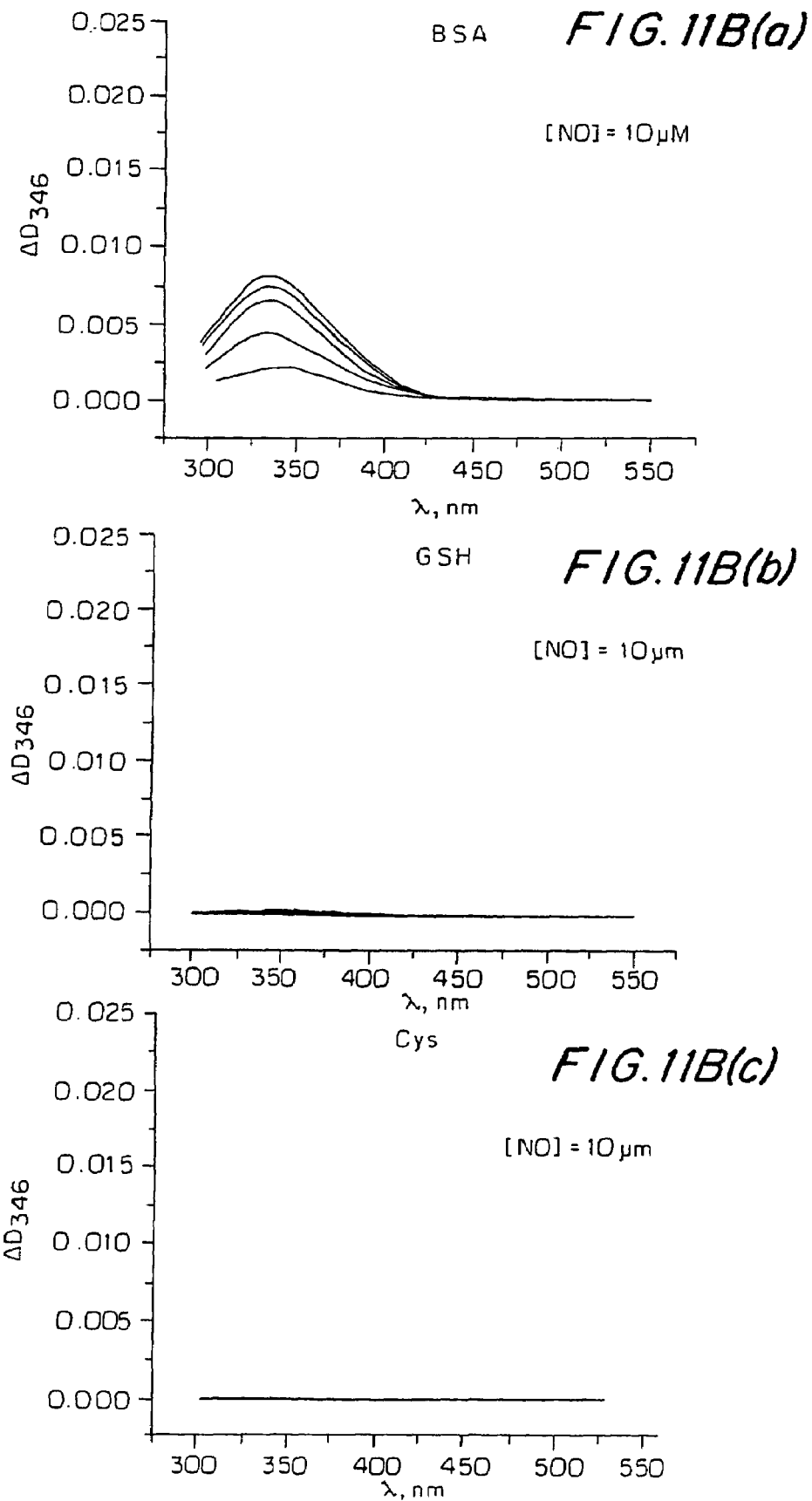

| BSA | + | + | + | + | − | − | − | − |
|---|---|---|---|---|---|---|---|---|
| 50% ANSA I / 50% ANSA II | − | + | + | + | + | + | + | − |
| NO μM | − | − | 10 | 50 | − | 10 | 50 | − |
| | ○ | ○ | ○ | ○ | ○ | ○ | ○ | ○ |
| F (%) | 5.6 | >>100 | 41.4 | 7.8 | 100 | 84.5 | 6.1 | 0 |
| | 1 | 2 | 3 | 4 | 5 | 6 | 7 | 8 |

| | | − | | | | | BSA | |
|---|---|---|---|---|---|---|---|---|
| %ANSA I | 50 | 0 | 25 | 50 | 75 | 100 | 50 | 50 |
| %ANSA II | 50 | 100 | 75 | 50 | 25 | 0 | 50 | 50 |
| NO μM | − | 50 | 50 | 50 | 50 | 50 | 10 | 50 |
| dye (II) — ANSA(II) — ANSA(I) — dye (I) — | | | | | | | | |
| | 1 | 2 | 3 | 4 | 5 | 6 | 7 | 8 |

NITROSATION-INDUCIBLE INHIBITORS BIOLOGICAL MACROMOLECULES

CROSS-REFERENCE TO RELATED APPLICATIONS

The present application is a continuation of Ser. No. 09/988,397, filed Nov. 19, 2001 now abandoned, which claims priority from provisional application Ser. No. 60/249,277, filed Nov. 17, 2000, the entire contents of which are hereby incorporated by reference.

FIELD OF THE INVENTION

The present invention relates to a method for inactivating biomacromolecules in order to regulate their metabolism. This method is particularly useful in combating pathogens and cancer cells.

BACKGROUND OF THE INVENTION

Nitric oxide (*NO) is an essential bioactive molecule that mediates a variety of actions, such as vasodilation, neurotransmission, and host defense. However, increased *NO production is often associated with the pathogenesis of various disorders, including cancer (Moncada et al, 1991; Kerwin et al, 1995). *NO is produced endogenously by a family of enzymes known as *NO synthases (NOS). Only the inducible isoform (iNOS) produces *NO concentrations in the micromolar range (Nathan, 1997), which is high when compared with the pico- to nanomolar concentrations produced by neuronal (nNOS) and endothelial (eNOS) isoforms (Brovkovych et al, 1999). iNOS is highly active in induced macrophages during chronic and acute inflammation causing excessive nitrosation (covalent attachment of nitroso group to thiols or amines) of proteins, lipids and nucleic acids—a condition known as nitrosative stress.

Recent studies indicate that the increases NOS expression and activity may contribute to tumor development or progression. High levels of *NO synthesis were observed in human gynecological (Thomsen et al, 1994), prostate (Klotz et al, 1998), breast (Thomsen et al, 1995), colon (Ambs et al, 1998), and central nervous system tumors (Cobbs et al, 1995). High levels of *NO are also observed in the most common chronic inflammatory diseases of digestive tract, which predispose individuals to cancer (Wilson et al, 1998; Mannick et al, 1996; Al-Mufti et al, 1998). Furthermore, most infectious bacteria produce a significant amount of NO endogenously and also become a subject to a macrophage-derived NO.

*NO is chemically unreactive toward most bioorganic compounds, but it spontaneously auotoxidizes to yield the highly reactive species, $N_2O_3$—the actual nitrosating agent (Williams, 1997; Kharitonov et al, 1995; Grisham et al, 1999) (FIG. 1A). Nitrosation of biological substrates occurs with high efficiency during nitrosative stress in body fluids and tissues (Grisham et al, 1999; Ischiropoulos, 1998). To explain the mechanism of nitrosation in vivo and particularly under noninflammatory conditions when the concentration of free NO is low, the mechanism of micellar catalysis of NO oxidation has been put forward (Liu et al, 1998; Nedosapasov et al, 2000). NO and $O_2$ are both hydrophobic molecules, areas of high hydrophobicity can act as a "sponge" to sequester them from the surrounding aqueous phase. High local concentrations of NO and $O_2$ in a hydrophobic phase, e.g. within lipid membranes, can significantly accelerate NO oxidation and $N_2O_3$ formation (Liu et al, 1998; Nedosapasov et al, 2000). Recently, we demonstrated that such micellar catalysis of NO oxidation occurs within the hydrophobic cores of various soluble proteins (Nedosapasov et al, 2000) (FIG. 1B). For example, serum albumin can accelerate the formation of $N_2O_3$ more than 15,000 times (Rafikova et al, 2001).

FIG. 1 shows micellar catalysis of *NO oxidation and nitrosation of biological substrates. FIG. 1 shows the third order reaction of *NO with $O_2$ ($k=6\times10^6 M^{-2} sec^{-2}$) (Wink et al, 1994). FIG. 1 shows hydrophobic compartments (micelles) formed by a protein globule accumulate *NO and $O_2$ from aqueous solution thus accelerating the formation of reactive nitrosating species, $N_2O_3$. $N_2O_3$ can react with water only at the surface of the protein (via intramolecular $NO^+$ transfer) to form nitrite ($NO_2^-$). At the same time, various nucleophiles (e.g. thiols [SH]) can penetrate the protein interior or exist already inside and be accessible for nitrosation (Nedosapasov et al, 2000).

SUMMARY OF THE INVENTION

It is an object of the present invention to overcome deficiencies in the prior art.

It is another object of the present invention to provide selective therapy to treat infections and cancer using ANSA derivatives.

It is a further object of the present invention to provide a method to inactivate a broad range of pathogens such as bacteria, fungi, viruses, by effecting nitrosation within the pathogen.

According to the present invention, specific hydrophobic compounds are provided which cooperate with *NO and oxygen to rapidly inactivate target proteins. These compounds are preferably aminonaphthalenesulfonamide (ANSA) derivatives which are precursors of compounds which are generated in vivo to inactivate proteins. These derivatives are hydrophobic and contain a peptidyl moiety which targets the derivative to a specific cell.

Formation of nitrosating $N_2O_3$ ($NO^+$—$NO_2^-$) within protein interiors does not necessarily lead to permanent protein nitrosation and damage, since the nitrosonium cation ($NO^+$) is readily transferred out of the protein globule into $H_2O$ to form relatively benign nitrite, as shown in FIG. 1B. However, with the help of additional small chemicals (ANSA), this process can be directed towards rapid protein inactivation.

The compounds of the present invention have three variable moieties chemically attached to ANSA, as shown below:

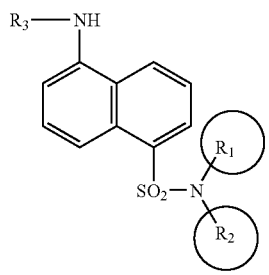

wherein at least one of $R_1$ and $R_2$ is a group which imparts hydrophobicity to the molecule and $R_3$ is either aminoacyl or peptidyl. $R_1$ and $R_2$ can be hydrogen $C_1$-$C_{30}$ alkyl, arylalkyl, alkylaryl, $C_1$-$C_{30}$ alkyl halide, alkenyl, and alkenyl halide. When $R_3$ is an aminoacyl group, the aminoacyl group generally has from about 1 to about 30 carbon atoms. Either $R_1$ or $R_2$ can be an affinity group for, e.g., a virus, such as a monoclonal antibody. When $R_1$ or $R_2$ is an affinity group, the other of $R_1$ or $R_2$ is selected such that the molecule is hydrophobic.

Groups which import hydrophobicity to the molecule, i.e., hydrophobic groups, include non-polar groups, such as $C_8$-$C_{30}$ alkyl, alkenyl, alkynyl, arylalkyl, and alkylaryl groups. One skilled in the art can readily determine what groups would impart hydrophobicity to the molecule.

The rate of nitric oxide-dependent nitrosation of hydrophobic aromatic amines in the presence of oxygen is increased in heterogenic media by micellar catalysis. The product of this reaction, aryldiazonium ion, is highly reactive, and rapidly interacts with biomacromolecules to inactivate these molecules. ANSA is superior to conventional hydrophobic aromatic amines because:

(1) ANSA can readily be manipulated to change the hydrophobic properties;

(2) conventional hydrophobic aromatic amines (e.g., aniline, naphthylamines) accumulate in mammalian organs (especially the liver) and form carcinogenic products upon oxidation. The presence of the sulfonamide group in ANSA prevents these compounds from accumulating because they are enzymatically hydrolyzed to sulfonic acid;

(3) coupling between amino and sulfonamide groups allows the formation of highly reactive aryldiazonium products;

(4) straightforward procedures for synthesizing ANSA and their derivatives have already been developed, particularly as described in USSR patents 1586902, 1814808 and 1648054.

As shown in FIG. 2A, nitrosation of the amino group converts the fluorescent ANSA into the aryl-diazonium cation that crosslinks to another ANSA molecule in solution or in the protein interior and loses its fluorescent activity. Coupling of two or more ANSA molecules produces non-fluorescent dyes. In FIG. 2 ANSA, $R_1$, $R_2$, and $R_3$ stand for variable substitutions. If $R_3$ is substituted the ANSA is unable to perform azocoupling reactions.

FIG. 2B shows the mechanism of ANSA-dependent protein inactivation. The hydrophobic ANSA molecules with an intact $NH_2$ group ($ANH_2$) accumulate inside the protein hydrophobic core and form reactive diazonium cations ($AN_2^+$) upon nitrosation. $AN_2^+$ crosslinks with nearby functional amino acids and inactivates the protein.

FIG. 2B illustrates the scenario. First, a protein solubilizes hydrophobic ANSA, and then the hydrophobic phase formed by nonpolar protein residues acts as an efficient micellar catalyst of *NO oxidation and formation of the nitrosating agent $N_2O_3$. Finally, if an $NH_2$ group of ANSA is available, the nitrosation reaction converts ANSA into the highly reactive aryl-diazonium cation that immediately crosslinks the protein interior. This suppresses the enzymatic activity of the protein.

According to the present invention, ANSA derivatives are administered to inactivate proteins using the nucleophilic $NH_2$ group in the ANSA as a suicide-nitrosative substrate. These compounds can be used as antipathogen or anti-cancer agents, and the selectivity and specificity of the compounds is determined by the peptide attached to the amino group, $R_3$. Peptidyl-ANSA molecules are resistant to activation by nitrosation until they have been transported into the cell and the target peptide has been cleaved by a particular protease or peptidase at the protein site. Because high concentrations of *NO are associated with host defense systems against microbial infections and some tumor cells as well, these molecules preferentially target those cells. Peptide transport and protease activities are species- or tissue-specific, such that the precise design of peptidyl-ANSA molecules permits selective therapy for infections or cancerous tumors.

Because the ANSA derivatives of the present invention inactivate proteins per se, they are particularly useful as broad-spectrum antibiotics, antifungals, and antivirals. The action of the ANSA derivatives depends solely on nitrosation, and therefore their action is not dependent upon the particular structure of the pathogen to be destroyed.

The hydrophobic derivatives of ANSA, with a free $R_3$ $NH_2$ group, can thus be used as suicide substrates for different enzymes in the presence of *NO and thus serve as a paradigm for the design of a new class of selective antibiotics. Since many enzymes can be targeted by these ANSA derivatives, the unique advantage of ANSA-based cytotoxins is that they can be designed to combat many different types of cells or proteins which are exposed to *NO or which produce *NO endogenously. Since there is a general positive relationship between the grade of malignancy and the amount of NOS content in tumors (Thomsen et al, 1994; Klotz et al, 1998; Thomsen et al, 1995; Ambs et al, 1998; Cobbs et al, 1995), including that of prostate tumors, ANSA will preferentially target cancer cells. It has been demonstrated that cancer cells are more sensitive to hydrophobic ANSA derivatives than are non-transformed cells in general, apparently because of higher endogenous *NO production by cancerous cells. The higher level of selectivity of ANSA compounds can be determined by which peptide is attached at the $R_3$ $NH_2$ group. Peptidyl-ANSA can be synthesized to be resistant to activation by nitrosation until transport into the cell or absorption to the cell membrane and the peptidyl ligand has been enzymatically removed, as shown in Figure Active peptide transport and protease activities are cell- or tissue-specific so that the precise design of peptidyl-ANSA molecules makes it possible to selectively target a particular cancer cell or a particular pathogen.

FIG. 5 shows that the peptide attached to the $R_3$ $NH_2$ group inactivates the ANSA. Enzymatic cleavage of the peptide inside the cell or on the cell surface enables the ANSA to be activated by nitrosation, crosslink to proteins, and kill the cell.

Another method of targeting ANSA to a particular pathogen is by using non-conventional or modified amino acid residues, such as D-amino acids, which are cleaved in prokaryotic cells but not in eukaryotic cells.

BRIEF DESCRIPTION OF THE DRAWINGS

FIG. 9 illustrates some ANSA derivatives.

FIGS. 11A-11B show comparative analysis of Trp nitrosation.

DETAILED DESCRIPTION OF THE INVENTION

ANSA derivatives are prepared to inactivate proteins upon nitrosation with NO and $O_2$ and, thus, can be used as antibiotics, antifungals, and antivirals and anti-cancer agents. The ANSA derivatives are designed to be specific to desired cells by altering the peptidyl substituents on the ANSA so that the derivative is selective to the particular pathogen or cancer cells to be targeted. Hydrophobic substituents are used to ensure that the derivatives are hydrophobic and are preferentially delivered to the hydrophobic site of a protein.

Figure 2A:
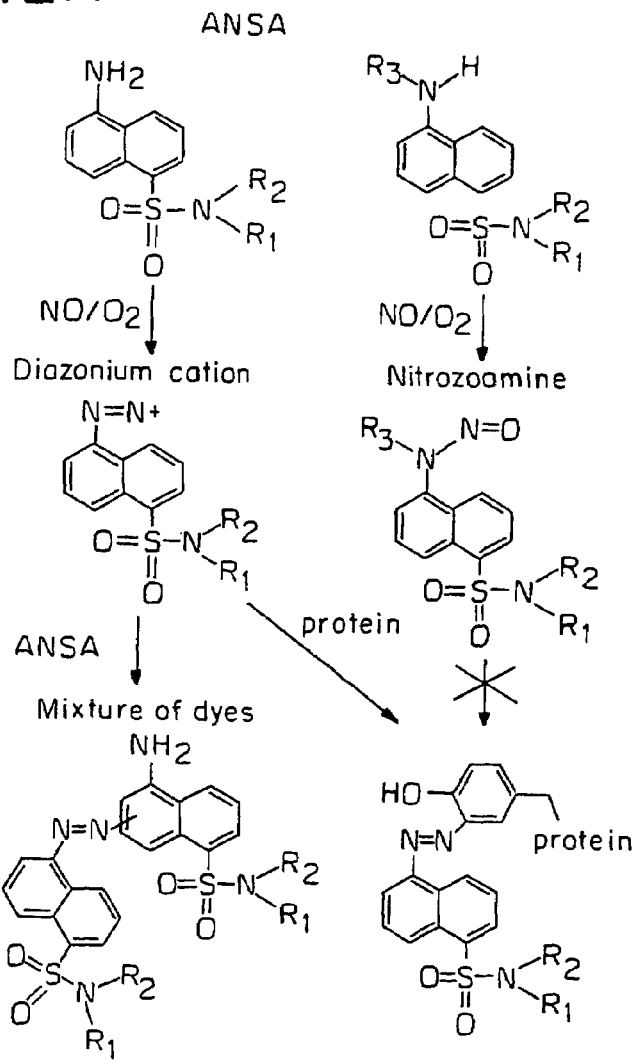
FIG. 2A shows the chemical structures and properties of 5-aminonaphthaline sulfonamides (ANSA).
Figure 2B:
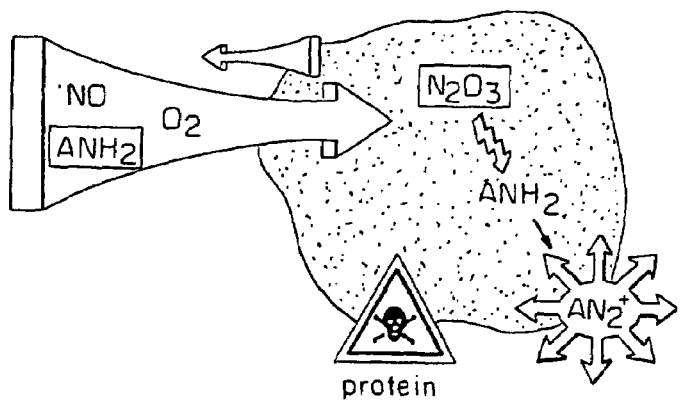
FIG. 2B shows the mechanism of ANSA-dependent protein inactivation.

As shown in FIG. 2B, agent ($N_2O_3$) first a protein solubilizes the hydrophobic ANSA. Then the hydrophobic phase formed by nonpolar protein residues acts as an efficient micellar catalyst of *NO oxidation and formation of the nitrosating agent. Finally, if an amino group of ANSA is free, the nitrosation reaction converts the amino group into a highly reactive aryldiazonium cation that immediately cross-links to the protein interior.

The hydrophobic compartments of proteins concentrate *NO and oxygen and, thus, catalyze formation of dinitrogen trioxide, $N_2O_3$, the primary nitrosating agent, as shown in FIG. 2B.

Experimental Procedures

*$NO/H_2O$ or *NO/DMSO solutions were prepared in the airtight device by bubbling *NO gas (Aldrich) that had been purified from higher oxides by passing it through a 1 M solution of KOH, into water or DMSO (Aldrich) until the concentration of dissolved *NO reached 1.2 mM. Water (Milli-Q grade) was deaerated by boiling and then cooling under argon (Praxair). The *NO concentration immediately before the reaction was measured by using ISO—NO Mark II nitric oxide electrode (WPI, Inc). DMSO was dehydrated by distillation in vacuum over CaO.

BSA, CM-BSA, GSH, Trp, Cys (Sigma) and the Trp-peptide (US Biological) were dissolved in water (1 mM stock solutions). The nitrosation reaction was carried out at room temperature in the 1 ml quartz cuvette. The blank probe contained 0.5 ml $K_2HPO_4/KH_2PO_4$ buffer (25 mM) pH=7.0 and 0.4 ml each of the tested reagent. 0.4 ml of an aqueous *NO solution was added for 5, 10, 15, 20, 25, or 30 minutes, then 0.1 ml of 0.1% ammonium sulfamate in 0.4N HCL was added for 1 minute to remove $HNO_2$ from the sample and UV-Vis spectra was recorded by using Ultrospec 3000 spectrophotometer (Pharmacia). Spectra were digitized and analyzed by Win DIG and Origin 6.0 software.

ANSA were synthesized from 5-nitronaphthalenesulphoacids and 5-aminonaphthalenesulphoacids (Reahim). TLC of ANSA and their derivatives was carried out on Silica gel 60 plates (Merck) in the hexane/ethyl acetate system. Gel filtration was performed using the Sephadex G25M size-exclusion column (Pharmacia). Fluorescence of ANSA was observed and measured under 365 nm UV light using BioRad Fluor-S MultiImager system.

Transcription reactions (total volume=20 µl) were performed in a buffer containing 20 mM Tris HCL, pH 7.5, 10 mM $MgCl_2$, 50 mM KCl, 8 µM ATP, GTP, UTP, 1.8 µM CTP, and 0.15 µM [$\alpha$-$^{32}$P] CTP (3000 Ci/mmol) for 5 minutes at 37° C. RNAP was purified as described (Nudler et al, 1996). The DNA template containing the A1 promoter of phage T7 was obtained by polymerase chain reaction from the plasmid pENtR2 (Nudler et al, 1996).

Figure 6:
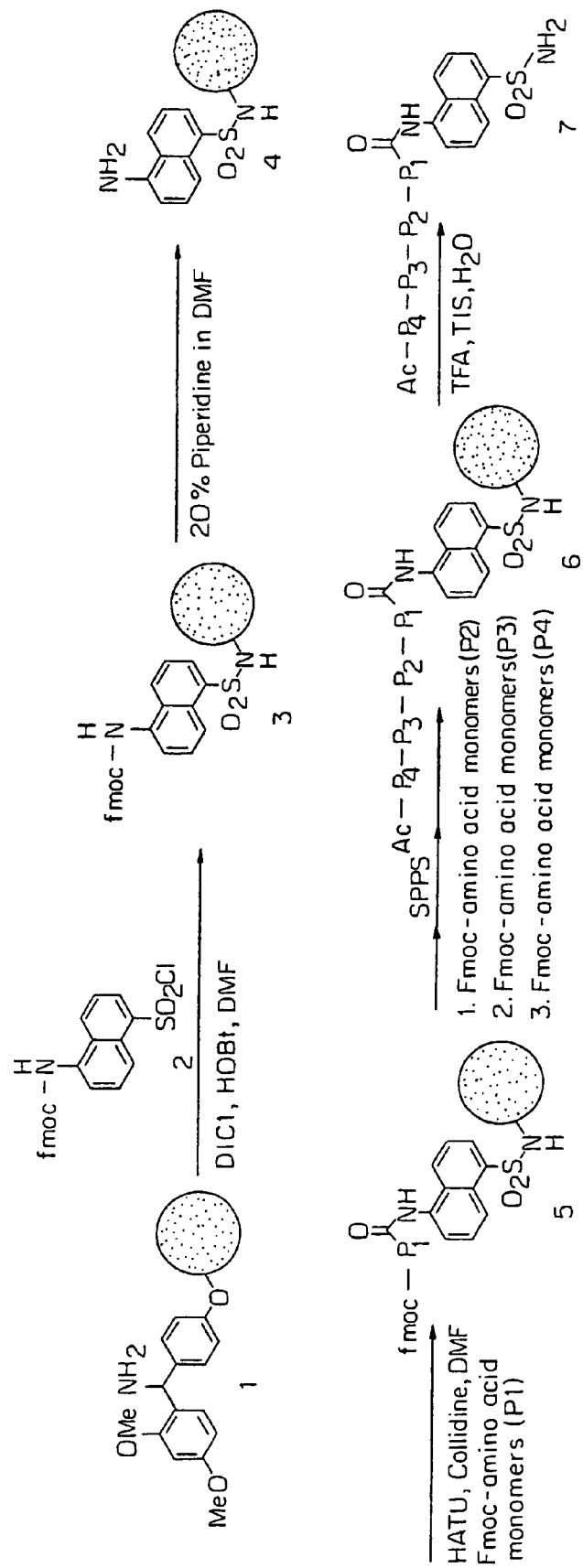
FIG. 6 illustrates synthesis of peptidyl-ANSA substrates.
Figure 7A:
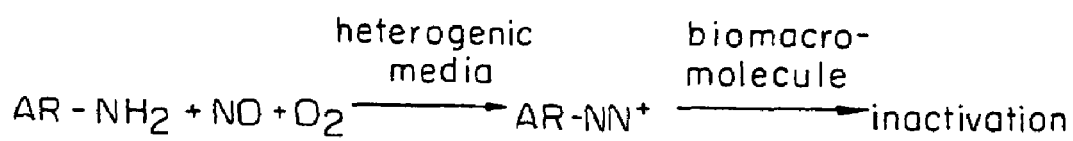
FIG. 7A shows reaction of inactivation of biomacromolecules by aromatic amines via micellar oxidative nitrosation.
Figure 7B:
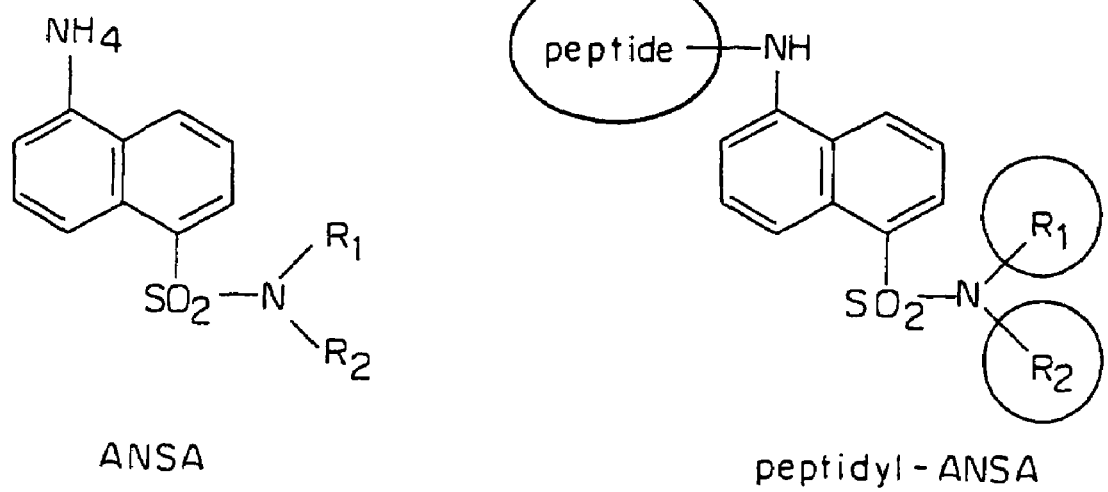
FIG. 7B shows aminonaphthalenesulfonamide (ANSA) and its peptidyl derivatives.

FIG. 6 illustrates synthesis of peptidyl-ANSA substrates by solid-phase peptide synthesis using standard 9-fluorenyl-methoxylcarbonyl (Fmoc) protocols. In FIG. 6, the circles stand for Rink Amide resin (Novabiochem), DMF is dimethylformamide, HATU is O-(7-azabenzotriazol-1-yl)-1,1,3,3-tetramethyluronium hexafluorophosphate, DICI is diisoproplycarbodiimde, HOBt is 1-hydroxybenzotriazole, TFA is trifluoroacetic acid, and TIS is triisopropylsilane.

Figure 12A:
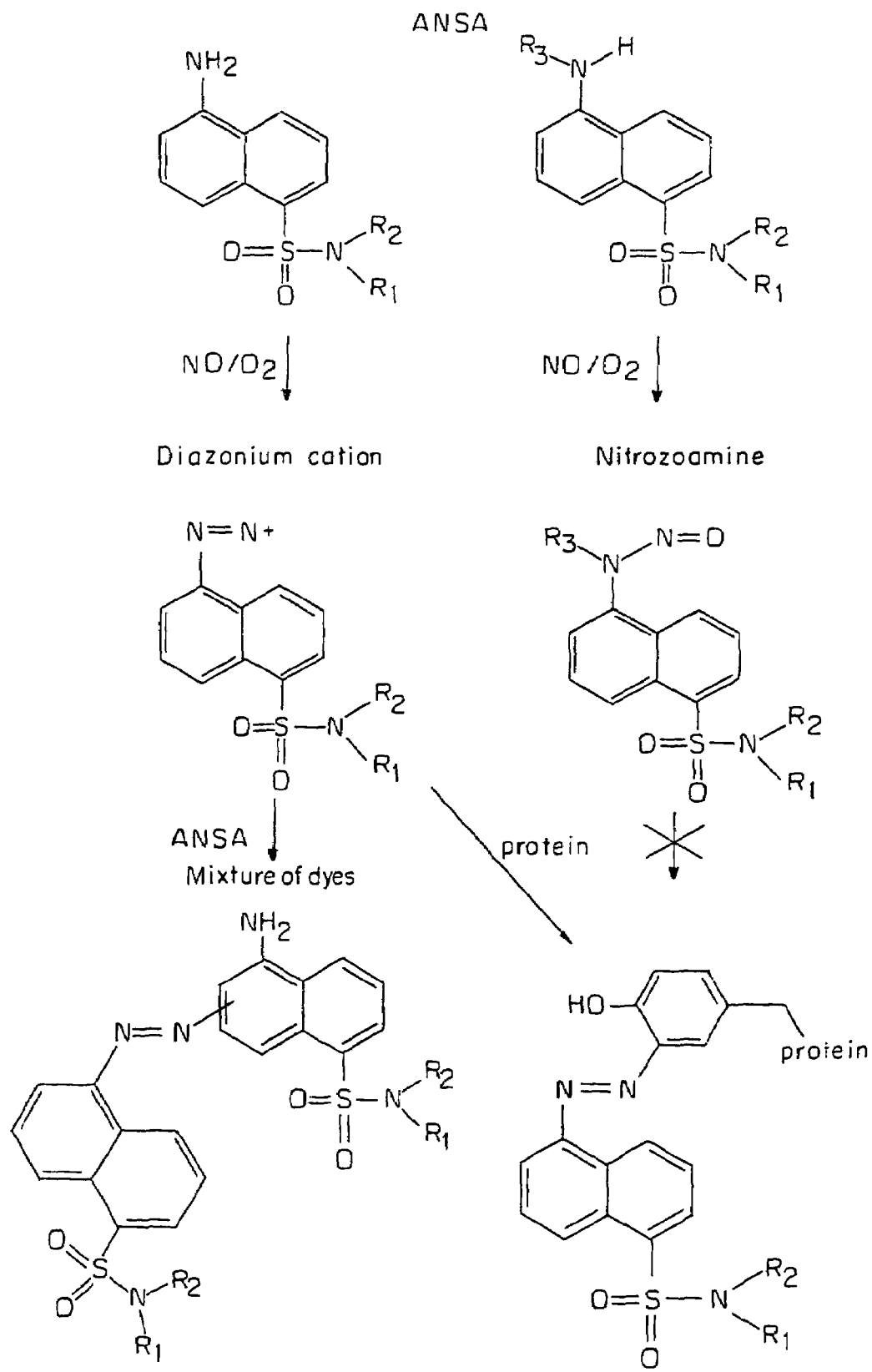
FIGS. 12A-12C illustrate NSA-mediated catalysis of ANSA nitrosation.

Protein Hydrophobic Core Is a Catalyst of Nitrosylation. The observed phenomenon of BSA-mediated catalysis of its own nitrosylation can be explained by the principle of micellar catalysis: the hydrophobic core of BSA accelerates formation of $N_2O_3$ by concentrating *NO and $O_2$ from water solution. To test this hypothesis directly the present inventors synthesized fluorescent versions of Griess indicators of nitrosation, 5-aminonaphthalene-sulfonamides (ANSA). ANSA are aromatic amines that contain a sulfonamide group with one or two aliphatic substitutions ($R_1$ and $R_2$) nitrosylation (Nedosapasov et al, 2000) (FIG. 12A). ANSA has a relatively low fluorescence yield in polar solvents, which is greatly enhanced in the nonpolar environment. Differences in the fluorescence activity can be readily visualized by the naked eye. Nitrosation of the $NH_2$ group converts the ANSA molecule to an aryldiazonium cation, which cross-links with another ANSA molecule (azocoupling reaction) to generate non-fluorescent deeply colored azoderivatives (FIG. 12A). The origin of each azoderivative dye can be defined by thin-layer-chromatography (TLC). Additionally, the hydrophobicity of ANSA can be changed by varying the identity of $R_1$ and $R_2$ groups.

Figures 12B, 12C:
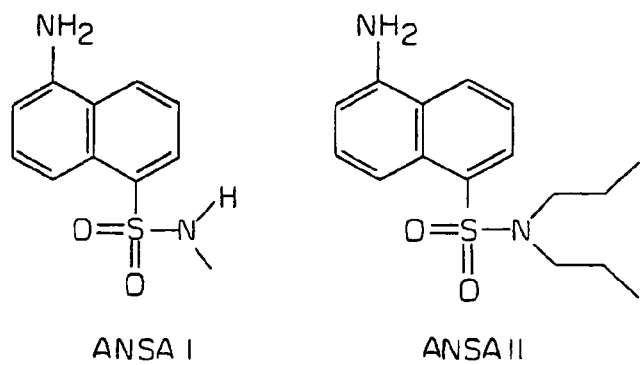

The present inventors first synthesized two ANSA with opposite hydrophobic properties (FIG. 12B). In the low-hydrophobic ANSA molecule (ANSA I), the $R_1$ group is —$CH_3$ and the $R_2$ group is —H. The highly hydrophobic ANSA (ANSA II) has $C_3H_7$ for both $R_1$ and RExperiments were done by mixing an aqueous solution of ANSA with the test protein, and then initiating the nitrosation reaction by the aerobic addition of an aqueous solution of *NO. Two initial concentrations of *NO were used at 25 molar excess over ANSA (high dose) and a 5 molar excess (low dose). In the absence of BSA, treatment of the ANSA I+ANSA II mixture with the high dose of *NO almost completely extinguished the fluorescence FIG. 4A at the same rate (FIG. 4B). It produced a set of dyes that accumulated proportionally and originated from both ANSA I and ANSA II (FIG. 12C, lane 4) indicating that both types of ANSA were nitrosated at the same rate. Under the same conditions, the low dose of *NO had little nitrosating effect since the fluorescence was decreased only slightly (FIG. 12B, lane 6). No nitrosation of ANSA under oxygen-free, argon conditions was observed, even when the high dose of *NO was applied (data not shown), indicating that the nitrosating agents must be intermediates of *NO oxidation. Since the pH of the reaction buffer was 7.5, it is likely that $N_2O_3$ rather then $HNO_2$ was the major nitrosating agent.

Figure 4A:
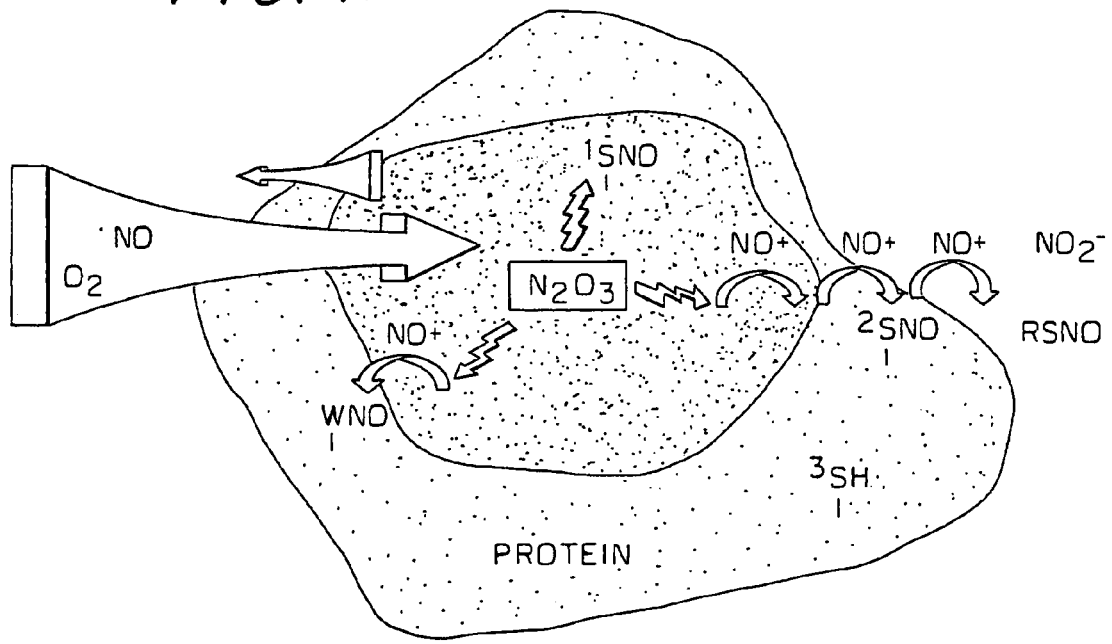
FIGS. 4A and 4B illustrate nitrosation of a test protein by aerobic addition of a solution of *NO.
Figure 4B:
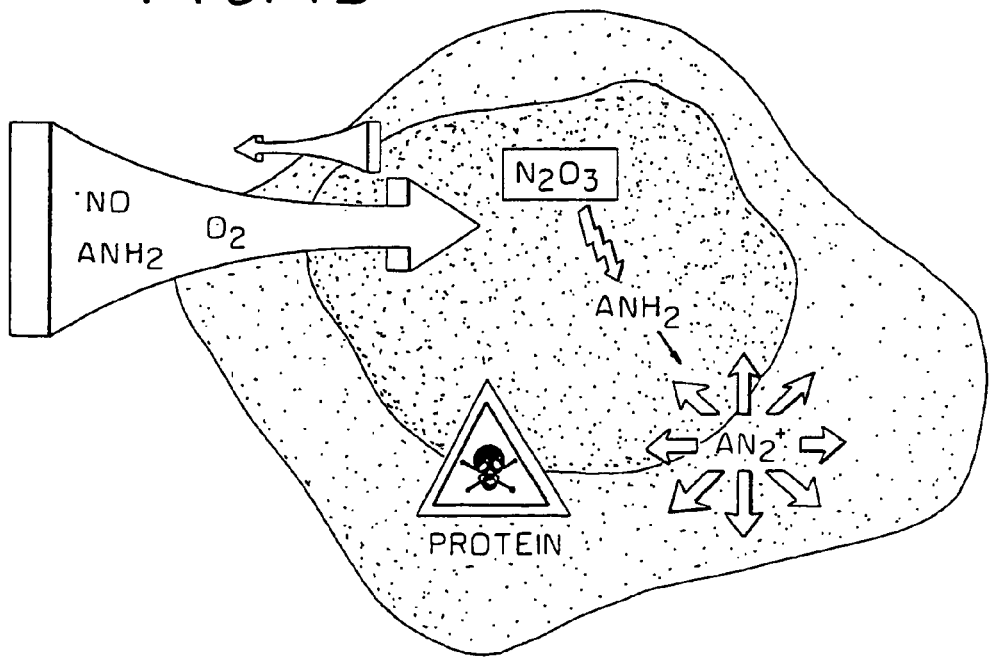
Figure 5:
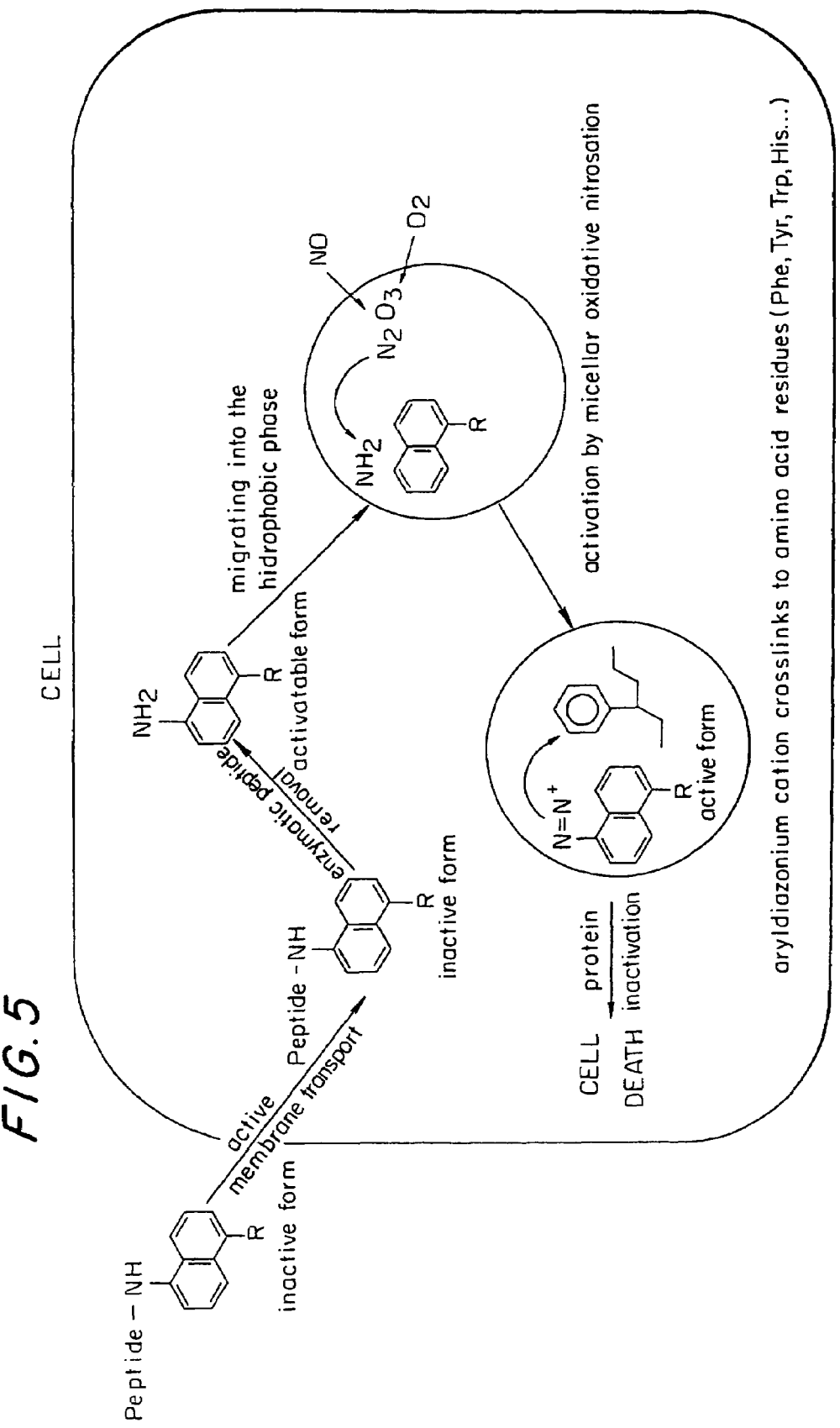
FIG. 5 shows peptidyl-ANSA as a selective *NO⁻ inducible chemotoxin.

In the presence of BSA, the results of nitrosation were completely different (FIG. 4A). ANSA II, but not ANSA I, was able to form a stable complex with BSA as evidenced by gel filtration analysis (not shown). Addition of BSA to the mixture of ANSA I+ANSA II increased the fluorescence of the solution significantly, (FIG. 12B, lane 2) indicating that ANSA II was solubilized by the hydrophobic core of BSA. The low dose of *NO was enough to decrease the fluorescence of the ANSA I+ANSA II+BSA mixture to approximately half that of the intact ANSA I+ANSA II mixture (FIG. 4A, compare lanes 3 and 5), indicating that approximately half the ANSA molecules became nitrosated. Since no dye formation with BSA and the low dose of *NO was observed (FIG. 12C, lane 7), it was concluded that only BSA-bound ANSA II, not free ANSA I, was nitrosated. This conclusion was confirmed by isolating intact ANSA I from the mixture by gel filtration and $CHCl_3$ extraction. The absence of ANSA II-generated dyes can be explained only if azoderivatives of ANSA II were cross-linked to amino acid residues of BSA and not to other ANSA molecules. Correspondingly, when the high dose of *NO was applied only dyes that originated from ANSA I were observed (FIG. 12C, lane 8). These results indicate that BSA acts as a catalyst of nitrosation of the bound hydrophobic compounds (ANSA II), i.e., the nitrosating activity appears to be greater in the hydrophobic interior of BSA then in solution.

The important conclusion from these observations is that various soluble proteins provide the environment for effective nitrosation of not only their own nucleophiles, but also of external molecules such as ANSA. Thus, the hydrophobic phase formed by plasma protein serves as a major reservoir of NO and its reactive oxides and plays an important role in maintaining the pool of RS-NO in vivo.

Hydrophobic Amines (ANSA) as *NO-Dependent Enzyme Inhibitors. To investigate whether this mechanism might be functioning in proteins other than BSA, the effect of nitrosation on a completely distinct protein—RNA polymerase from E. coli (RNAP)—was examined. The experiments were done by exposing RNAP to a low dose of *NO, and then adding the DNA template and ribonucleotide substrates to initiate the transcription reaction. For a control, a solution of $NO_2^-$ for the *NO was substituted by oxidizing *NO prior to the experiment. As FIG. 3 shows, *NO partially inhibited transcription (lane 2) while $NO_2^-$ had no effect (lane 3). The *NO-dependent inhibition of RNAP was complex. Nitrosation of the RNAP decreased the overall amount of transcripts, suggesting that the early steps of transcription cycle were suppressed (e.g., DNA binding and open promoter complex formation). Additionally, the addition of *NO decreased significantly the accumulation of the full-length, 49 nt. transcript. Shorter transcripts represent paused RNAP molecules resulting from the limited amount of CTP in the reaction. This redistribution of RNA transcripts upon nitrosation suggests that the catalytic parameters of RNAP ($K_m$ for ribonucleotides and/or $V_{max}$) have been changed. The complex inhibitory effect of nitrosation on RNAP is not surprising since many potential nitrosation targets are distributed in structurally and functionally distinct regions of the enzyme (Zhang et al, 1999).

The experiments with BSA demonstrated that upon nitrosation, ANSA II could cross-link to its "host" protein molecule. To determine whether this process could also occur with RNAP, the mixture of RNAP+ANSA II was treated with *NO (FIG. 3, lane 4). In the presence of ANSA II, the same low dose of *NO as used in lane 2 completely inactivated RNAP. ANSA II alone did not affect transcription (lane 5).

Figures 3A, 3B:
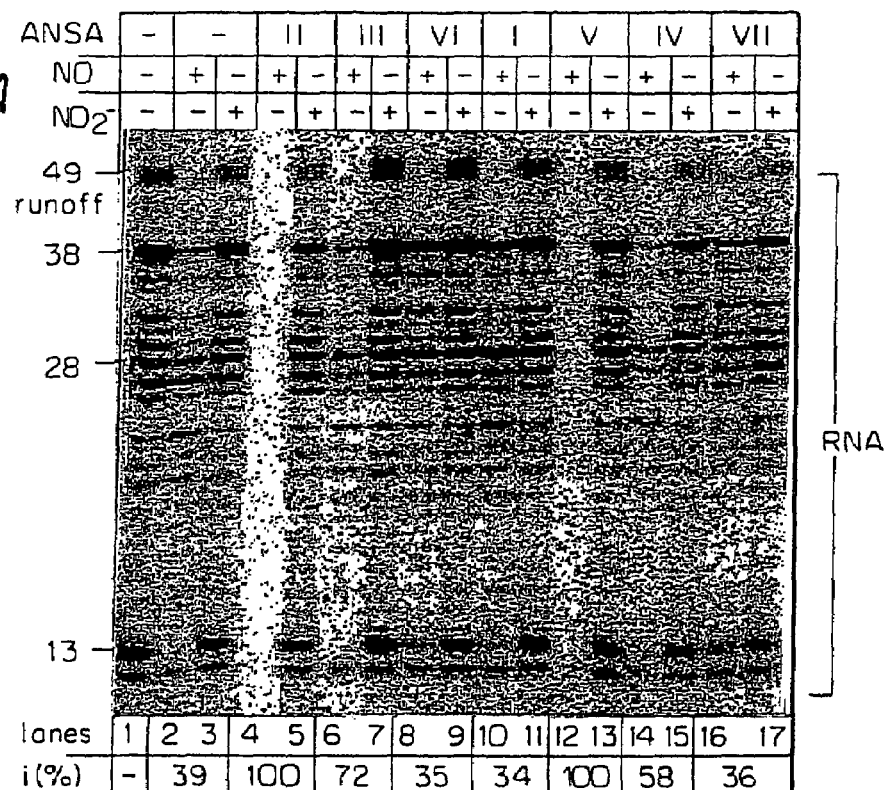
FIGS. 3A and 3B show inactivation of *E. coli* RNA polymerase by *NO and ANSA derivatives (Nedosapasov et al, 2000).

To further test the autocatalytic mechanism of enzyme inactivation and the key role of nitrosation-azocoupling in this process additional ANSA was synthesized and were tested in the *NO-dependent RNAP inactivation assay (FIG. 3). FIG. 3B shows ANSA that were designed to have different degrees of hydrophobicity (I<III≈IV<VI<V≈VII<II). It was found that the hydrophobicity of ANSA directly correlated with its ability to stimulate the *NO-dependent inactivation of the enzyme. The least hydrophobic ANSA I had no effect on transcription (lane 10), ANSA III and ANSA IV exhibited a partial negative effect (lanes 6 and 14), and ANSA V completely inactivated RNAP (lane 12). ANSA VI and ANSA VII, with methyl and peptidyl substitutions in the $NH_2$ group, were incapable of forming aryldiazonium cation upon nitrosation. Although ANSA VI and ANSA VII were more hydrophobic then ANSA III and ANSA IV, they were unable to enhance inactivation of RNAP (lanes 8 and 16). This experiment raises the possibility that hydrophobic amines could be used as efficient tools for the *NO-dependent inactivation of enzymes.

The results with ANSA can be described by the following scheme (FIG. 2B). First, a protein solubilizes hydrophobic ANSA. Then, the hydrophobic phase formed by nonpolar protein residues acts as an efficient micellar catalyst of *NO oxidation and formation of the nitrosating agent. Finally, if an $NH_2$ group of ANSA is free, the nitrosation reaction converts it into highly the reactive aryldiazonium cation that immediately cross-links to the protein interior and suppresses the enzymatic activity.

Figures 1A, 1B:
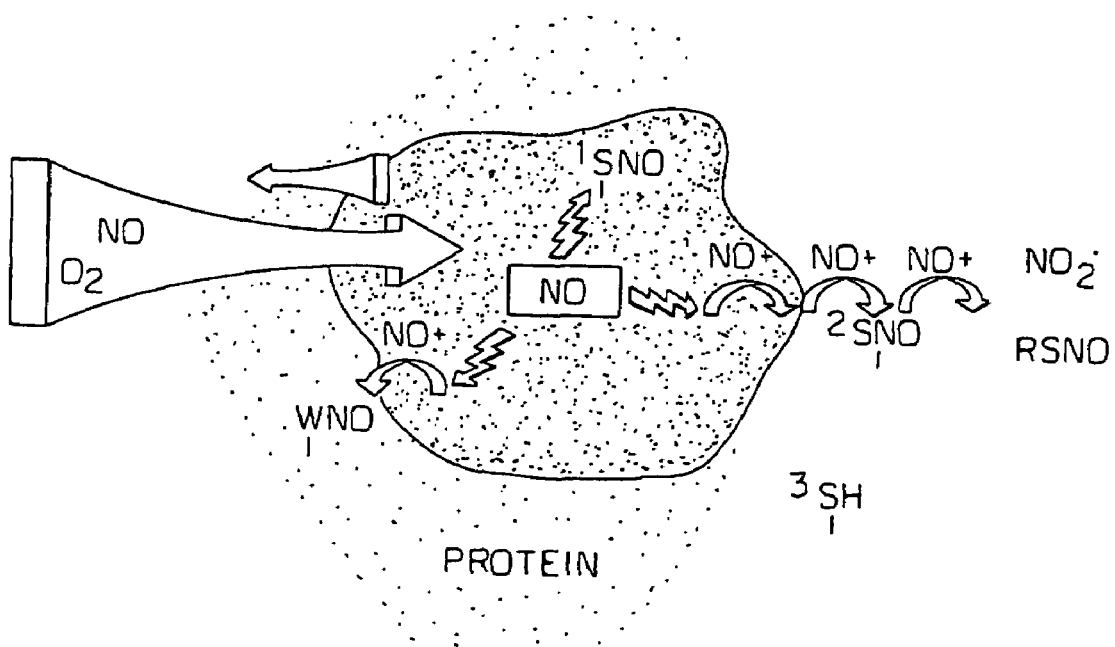
FIGS. 1A and 1B show micellar catalysis of *NO oxidation and nitrosation of biological substrates (e.g., proteins).

The data obtained above suggest a mechanism in which hydrophobic compartments of proteins concentrate *NO and $O_2$ and, thus, catalyze formation of $N_2O_3$, the primary nitrosating agent (FIG. 1). As soon as $N_2O_3$ is formed within the protein interior, it attacks nearby nucleophilic amino acid groups. Short-lived intermediates of this reaction transfer the nitroso-group further to less nucleophilic competitors and finally to molecules of water or thiols in the surrounding media. This model, by which nitrosating agents are created in regions of hydrophobicity, accounts for the high selectivity of S-nitrosylation protein modifications (Stamler et al, 1998). In this case the overall structure of the protein (the size and geometry of the hydrophobic core and distribution of nucleophiles) determines its ability to generate $N_2O_3$ and also transfer $NO^+$ to a particular Cys targets.

According to this model, $N_2O_3$ is synthesized not only during nitrosative stress, i.e., when the concentration of *NO donors in solution rises substantially (Grisham et al, 1999; Espey et al, 2000; Stamler et al, 1998, and references therein), but constitutively in the hydrophobic protein interior where the local concentration of *NO and $O_2$ is much higher then in solution. Thus, the concentration of $N_2O_3$ depends not only on the initial concentrations of *NO and $O_2$ in the whole system, but also on the size and geometry of the hydrophobic phase, as well as the distribution of available targets in the protein molecule. Such a mechanism further suggests that both S-nitrosylation and N-nitrosation can be controlled not only by the activity of NO-synthases and $O_2$ concentration but also by conformational transitions in the protein molecule that change its hydrophobic properties. Additionally, nitros (yl)ation itself may be able to induce further conformational transitions, which may be favorable or unfavorable to continue the process. Further, the solubilization of hydrocarbons and other hydrophobic compounds by proteins could affect nitrosation due to the increased efficiency of micellar catalysis.

In vivo, protein-mediated catalysis of *NO oxidation is likely to compete with a similar process within lipid membranes (Goss et al, 1999). It is remained to be determined which reaction and under what conditions contributes most to the formation of primary nitrosative species at the cellular and subcellular levels.

As is shown here, BSA and RNAP provide the environment for effective nitrosation of not only their own nucleophiles but also external molecules such as ANSA. In a separate study (R. Rafikov, Olga Rafikova, and E. Nudler, manuscript in preparation), it demonstrated that albumin significantly stimulates formation of vasoactive low-molecular-weight nitrosothiols via the mechanism of micellar catalysis. $Q_{NO}$ for BSA/$H_2O$ was determined to be ≈2. Taken together, these data suggest that the hydrophobic phase formed by plasma protein serves as a major reservoir of *NO and its reactive species and plays an important role in maintaining the pool of RS—NO in vivo.

Figure 8:
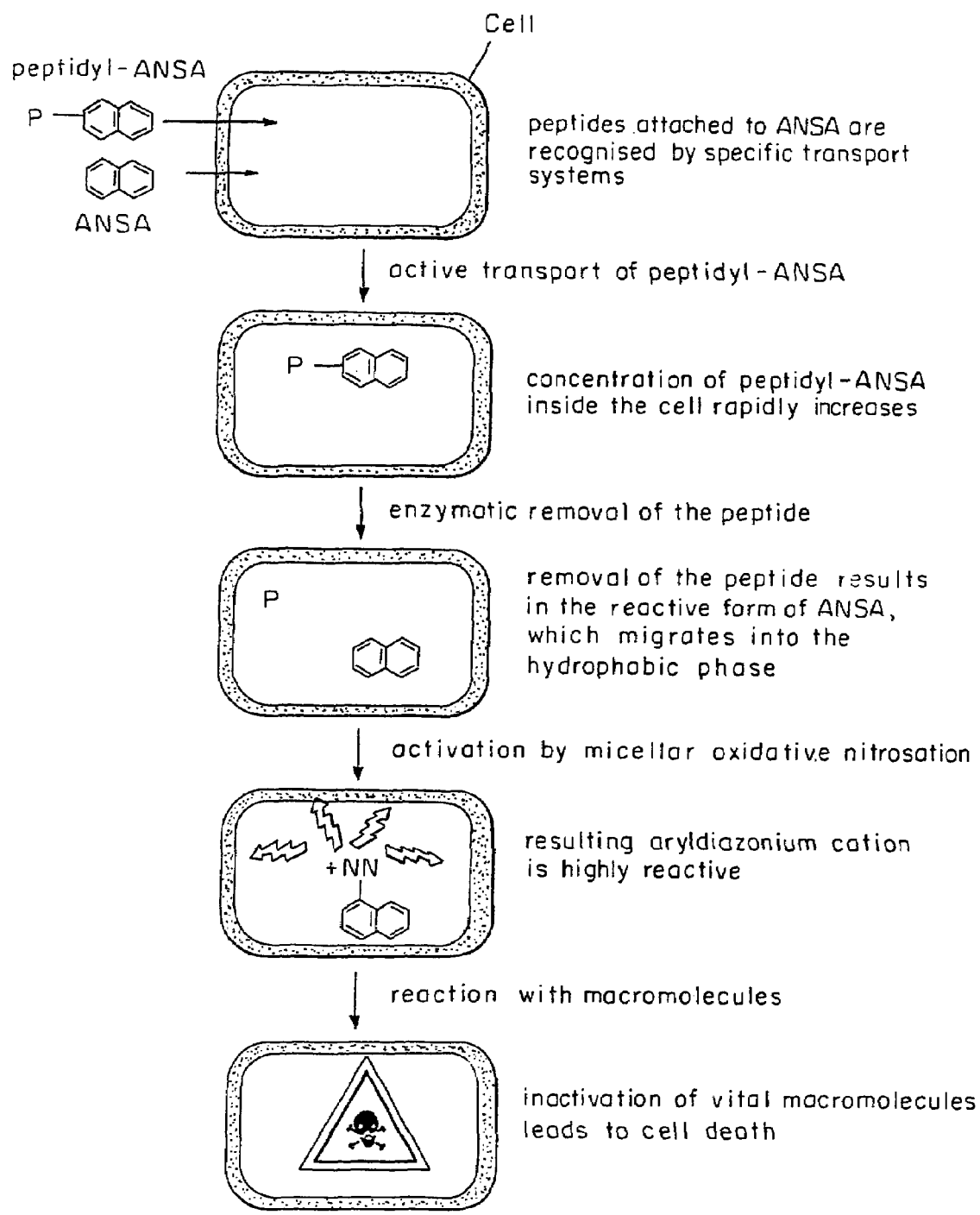
FIG. 8 illustrates how peptidyl-ANSA acts as a NO⁻ dependent antibiotic.
Figure 10A:
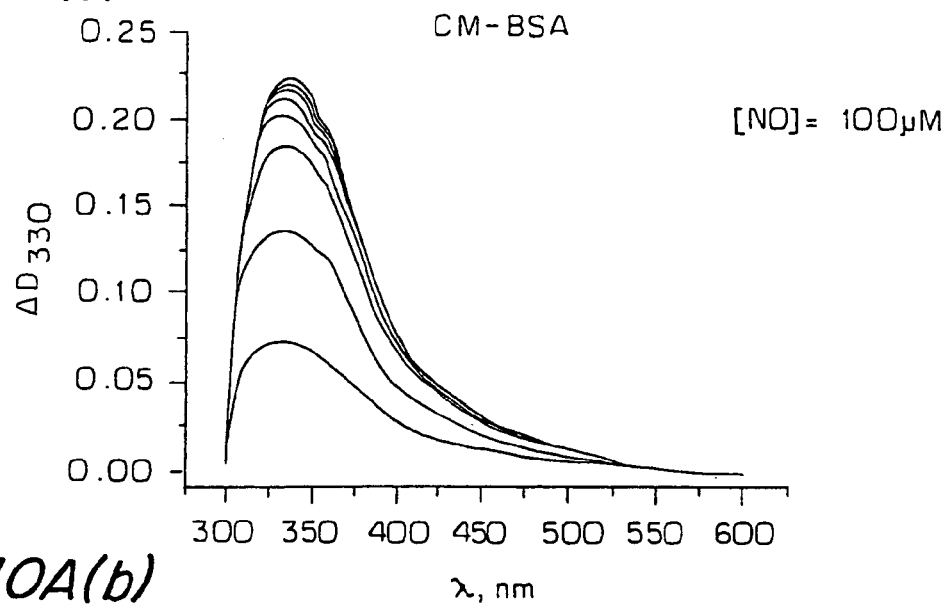
FIGS. 10A-10D show comparative analysis of Cys nitrosation.
Figure 10A:
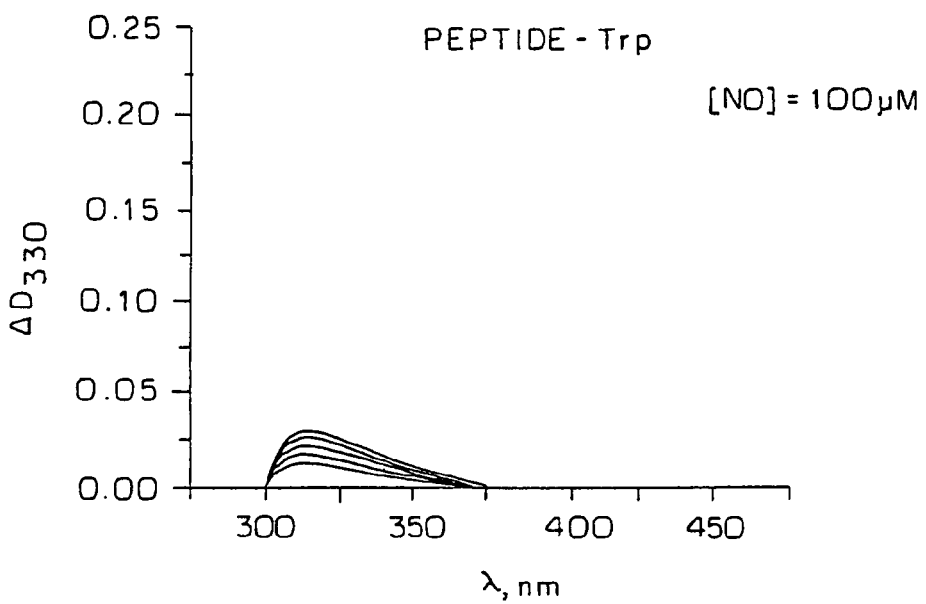
Figure 10B:
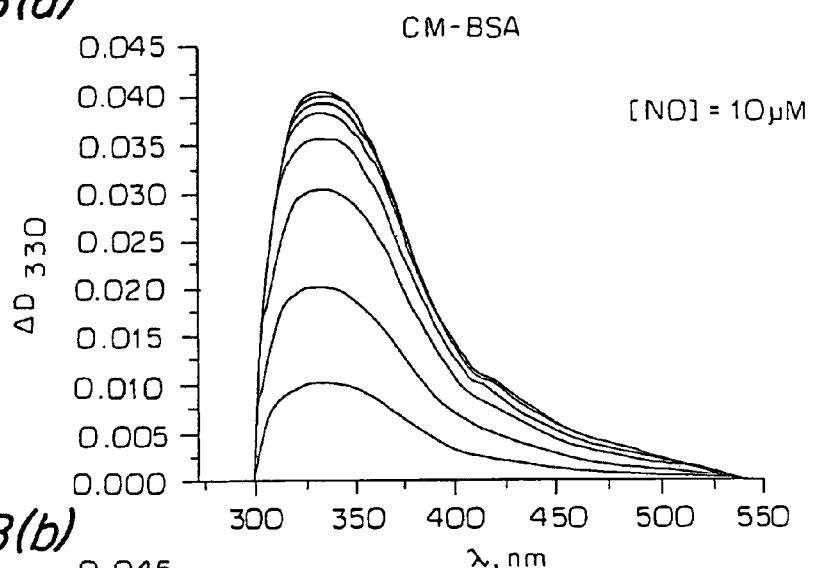
Figure 10B:
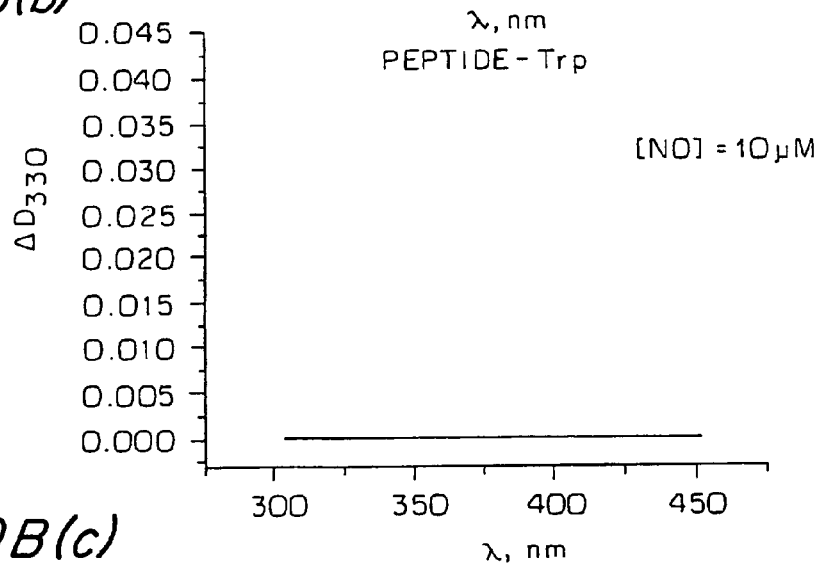
Figure 10B:
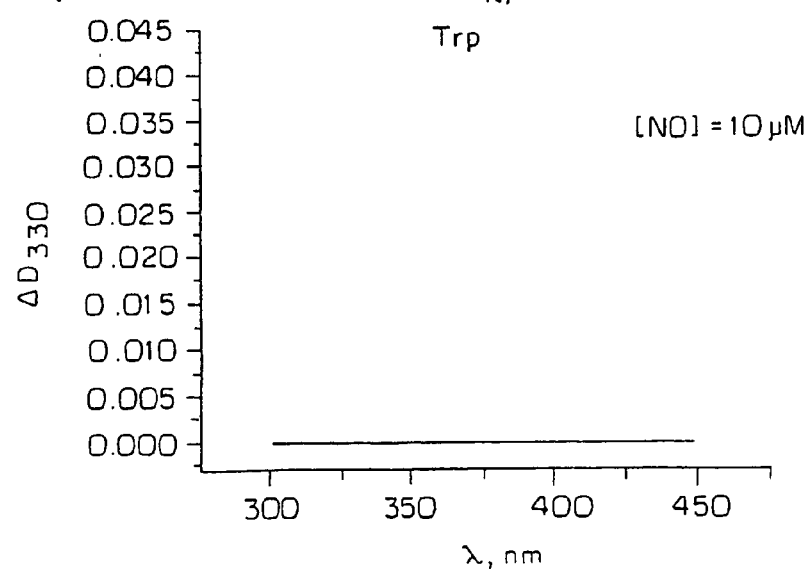
Figure 10C:
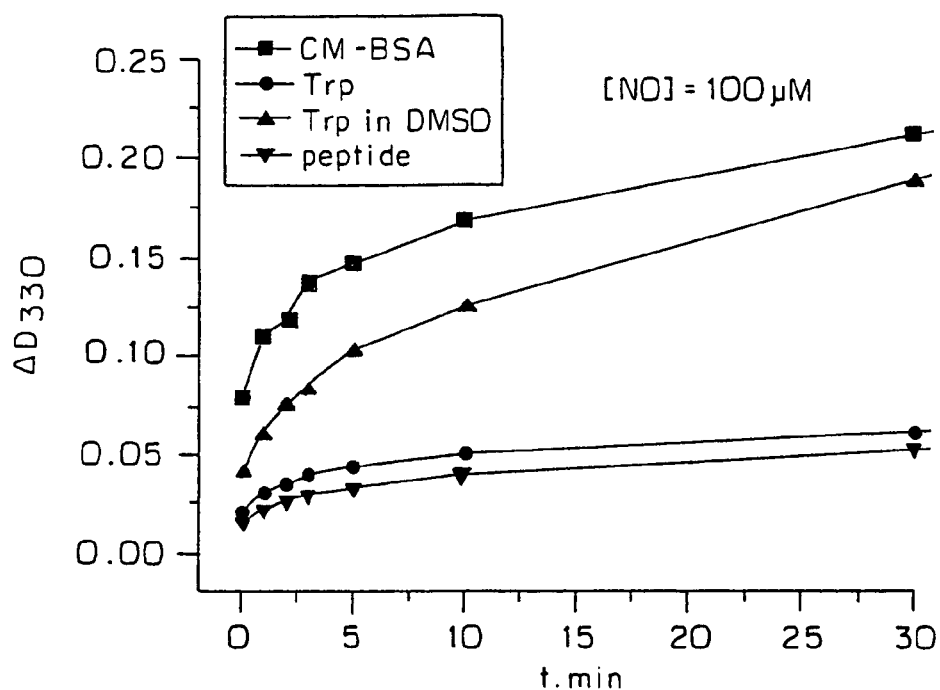
Figure 10D:
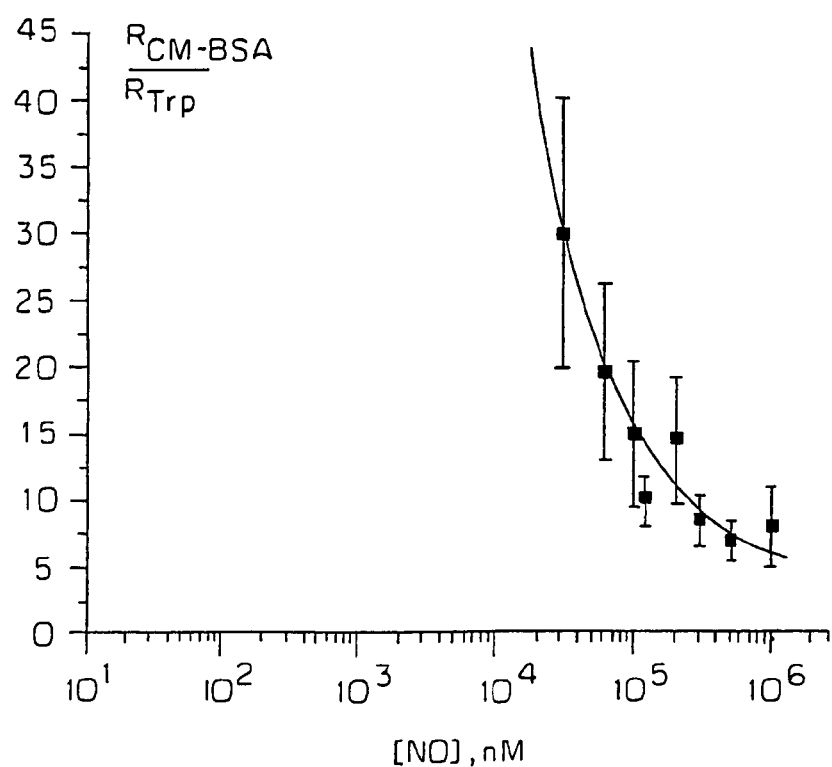

Here it is demonstrated that the ability of a protein to accelerate nitrosation can be directed towards its own inactivation. ANSA molecules with the nucleophilic $NH_2$ group can be used as a suicide nitrosative substrate for different proteins and, thus, can serve as a paradigm for the design of a new class of antibiotics. The high selectivity and specificity of such compounds can be determined by the peptide attached to the $NH_2$ group (FIG. 8). Peptidyl-ANSA molecules can be synthesized which are resistant to activation by nitrosation until they have been transported into the cell and the peptide has been cleaved by a particular protease or peptidase. Since high concentrations of *NO are associated with host defense systems against microbial infections and also some tumor cells, such molecules would preferentially target those cells. Peptide transport and protease activities are species- or tissue-specific so that the precise design of peptidyl-ANSA molecules allows the exciting possibility for new kinds of selective therapy. One skilled in the art can, without undue experimentation, readily design peptidyl-ANSA molecules that can target a desired protein so as to target specific bacteria, viruses, fungi, cancer cells, etc.

ANSA Derivatives as a New Class of Antibiotics and Antineoplastic Drugs. ANSA derivatives (shown in FIG. 9) were tested for their cytotoxic capabilities using wild type strains of Gram-negative and Gram-positive bacterial (*Escherichia coil* strain BL21 and *Bacillus subtilis* Strain IS75). As Table 1 shows, hydrophobic ANSA exhibited strong bactericidal effects, which directly correlated with the amount of NO produced by different bacteria under various growth conditions. NO trap, 2-phenyl-4,4,5,5-tetramethylimidazoline-1-oxyl-3-oxide (PTIO), almost completely abolished the inhibitory effect of ANSA on the amount of colony forming units (CFU), while addition of a water solution of NO restored the bactericidal effect of ANSA, thus indicating that the toxicity of ANSA was strictly dependent upon nitrosation. Aliphatic $R_1$ and $R_2$ substitutions, as well as the $R_3$ $NH_2$ group, were essential for growth inhibition. ANSA VIII that contained a non-cleavable $R_3CH_3$ had no effect on cell survival. Notably, ANSA with a peptidyl $R_3$ substitution (ANSA VII) exhibited the strongest bactericidal effect.

TABLE 1

Bacterial Properties of Different ANSA Derivatives

| | E. coli | | B. subtilis | | |
|---|---|---|---|---|---|
| | rich | minimal | rich | minimal | media |
| — | ≈$10^7$ | ≈$10^7$ | ≈$10^7$ | ≈$10^7$ | CFU $ml^{-1}$ |
| *NO | ≈$10^6$ | ≈$10^6$ | ≈$10^6$ | ≈$10^6$ | |
| ANSA 1 | $10^6$-$10^7$ | ≈$10^7$ | ≈$10^7$ | ≈$10^7$ | |
| ANSA V | 0-20 | ≈$10^3$ | $10^2$-$10^3$ | $10^2$ | |
| ANSA VII | 0 | ≈ | | | |
| ANSA VIII | ≈$10^7$ | ≈$10^7$ | ≈$10^7$ | ≈$10^7$ | |
| ANSA V + *NO | 0 | 0 | 0 | 0 | |
| ANSA V + PTIO | ≈$10^5$ | ≈$10^5$ | $10^5$-$10^6$ | ≈$10^5$ | |
| ANSA V + *NO + PTIO | 5-10 | 0.05-0.2 | 1-2 | ≈2 | [NO] µM |

Data were collected from three independent experiments. In each case cultures in the early exponential phase of growth ($10^7$ CFU $ml^{-1}$) were treated with 20 µg/ml ANSA derivatives for 30 minutes at room temperature without shaking in either LB broth (rich media) or M9 (*E. coli*) or Spizizen's (B.s.) minimal medias. As indicated, *NO aqueous solution and/or PTIO were added as bolus to the final concentration of 20 µM each. ANSA VIII is the same as ANSA V but with a $CH_3$ substitution at $R_3$.[*NO] was measured directly in growing cultures by using a Clark-type NO-electrode.

A second preliminary study used two human hormone-independent prostatic carcinoma cell lines DU-145 and PC-3 (ATCC, Virginia) and normal human fibroblasts (WI-38). The MTS cytotoxicity assay ("CellTiter 96", Promega) was used to measure the cytotoxicity of several ANSA compounds in the presence or absence of *NO. All compounds tested in vitro were dissolved in DMSO (100 µM solution) and subsequently diluted in the culture medium before treatment of the cultured cells. Tested cells were plated in 96-well plates at a density of $4 \times 10^3$ cells/well/200 µL of the proper culture medium and treated with the compounds at concentrations of 0.1-100 µM. In parallel, the cells were treated with 1% of DMSO as control. MTS assay was performed 72 h later according to instructions provided by the manufacturer (Promega). This assay is based on the cellular conversion of the tetrazolium salt, MTS[3-(4,5-dimethylthiazol-2-yl)-5-(3-carboxymethoxyphenyl)-2-(4-sulfophenyl)-2H-tetrazolium, inner salt], into a formazan that is soluble in cell culture medium and is measured at 490 nm directly in 96-well assay plates without additional processing. Absorbency is directly proportional to the number of living cells in culture.

Hydrophobic ANSA, but not hydrophilic ANSA I, exhibited a strong cytotoxic effect, which directly correlated with the amount of exogenous *NO provided. In one control, the NO trap, 2-phenyl-4,4,5,5-tetramethylimidazoline-1-oxyl 3-oxide (PTIO), was used, which decreased the inhibitory effect of *NO in the presence of ANSA, thus indicating that the toxicity of ANSA strictly depended on nitrosation. Since, the general NOS inhibitor, L-NAME, also decreased the cytotoxicity of ANSA it was concluded that endogenous production of *NO in prostate cancer cells at least partially is responsible for intrinsic ANSA cytotoxicity. Aliphatic $R_1$ and $R_2$ substitutions as well as the $R_3$ $NH_2$ groups were essential for cell growth inhibition. ANSA VIII, which is the same as ANSA V but contained a non-cleavable $R_3$ $CH_3$, had no effect on cell survival. Notably, ANSA with a peptidyl $R_3$ substitution (ANSA VII) (FIG. 9) exhibited the strong cytotoxic effect. In order to be nitrosated, peptidyl-ANSA must undergo cleavage of the C-terminal amino acid residue to relieve the $R_3$ $NH_2$ group. Taking advantage of the chromogenic nature of ANSA compounds we were able to determine whether the peptidyl-ANSA were transported in the cell and/or bound to the cell membrane and processed by proteolysis. During incubation with ANSA VII cultured cells turns yellowish. After cell disruption followed and sedimentation much of yellow stain remained in the supernatant. Yellow dye formation is indicative of the azocoupling reaction between ANSA molecules (FIG. 2A) suggesting that the peptidyl group indeed had been removed and that nitrosation occurred intracellular or in the membrane.

In order to be nitrosated, peptidyl-ANSA must undergo cleavage of the C-terminal amino acid residue to relieve the $R_3$ $NH_2$ group. Taking advantage of the chromogenic nature of ANSA compounds, it was possible to determine whether the peptidyl-ANSA were transported in the cell and processed by proteolysis. During incubation with ANSA VII, *E. coli* cells turned deeply yellow. After mild cell disruption followed by sedimentation of the membrane debris, much of the yellow stain remained in the supernatant. Yellow dye formation is indicative of the azocoupling reaction between ANSA molecules, suggesting that the peptidyl group had indeed been removed and that nitrosation occurred intracellularly. Unlike most common bacteriotoxic antibiotics, ANSA derivatives kill bacterial cells extremely rapidly. Minimal inhibitory concentrations of ANSA derivatives were comparable with that of most standard antibiotics.

ANSA derivatives also can be used to kill viruses, fungi, and other pathogens extremely rapidly by inactivation of these proteins. Minimal inhibitory concentrations of the ANSA derivatives can be used as antifungals, antivirals, etc. because of the rapid action of these compounds.

Thus, the ANSA derivatives of the present invention are designed to target proteins and suppress enzymatic activities of these proteins upon nitrosation. While these compounds are particularly useful as bactericides and anti-tumor compounds, they also are effective against any other types of biomacromolecules that are undesirable, including but not limited to viruses, enzymes, toxins, and the like. The peptidyl moiety can be designed to recognize a specific protein receptor, and the hydrophobic groups help directed the ANSA derivative to the appropriate location in the protein.

The ANSA derivatives of the present invention are hydrophobic derivatives of 5-aminonaphthalenesulfonamides with a free amino group which is coupled to a peptidyl group. These compounds are used as a suicide nitrosative substrate for different enzymes, including bacterial RNA polymerase and beta-galactosidase and, thus, can be used as a new class of antibiotics. Since virtually any enzyme can be targeted by the ANSA derivatives, the unique advantage of using the ANSA derivatives of the present invention is that they can be designed to combat diverse types of cells, including bacteria, and cancer cells as well as diverse types of viruses.

Many infectious bacteria constitutively produce substantial amounts of NO via enzymatic reduction of nitrite/nitrate. On the other hand, there is a general positive relationship between the grade of malignancy and the amount of NOS in tumors. Furthermore, the high level of inducible NO is generally associated with host defense against microbial infections as well as cancer cells, and ANSA derivatives can be designed to target those cells specifically.

The most common infectious bacterial species, including *Staphylococcus* spp., *Escherichia coli, Mycobacterium,* and *helicobacter pylori,* are facultative anaerobes that use nitrate/nitrite besides oxygen as an electron acceptor or oxidation of carbon compounds to derive energy under microaerobic conditions. NO is an intermediate in the process of denitrification formed by the action of the respiratory nitrite reductases cytochrome cd1 or copper nitrite reductase.

Tumor cells are usually characterized by increased intracellular and extracellular levels of NO produced by their own NOS as well as iNOS of activated tumor invading macrophages. They are also characterized by hyperactive extracellular proteolysis. In particular, the extracellular matrix metalloproteinases and the serine proteinase, urokinase-type plasminogen activator, are most extensively linked to cancer invasions and metastasis. Superposition of two selective factors, high local concentration of NO and intensive proteolysis, provides an opportunity for ANSA-based chemotherapy. However, unlike the situation with bacteria, in order to be activated peptidyl-ANSA need not necessarily be transported inside the cell, but rather inserted into the membrane via $R_1/R_2$ aliphatic tails. The exposed peptidyl substrate is then available for extracellular proteolysis.

To construct selective peptidyl variations of ANSA, a non-random approach includes incorporation of peptidyl groups that have been previously selected as specific substrates for the metastasis associated proteases. For example, a specific substrate for uPA, $NH_2$-Asp-Thr-Ala-Arg-X, has been selected from the synthetic library of 137,180 substrate members. Another peptide, $NH_2$-Gly-Pro-Leu-Gly-/X, was selected from a phage display library containing $2 \times 10^8$ independent recombinants as a specific substrate for MMP-13. These and other specific peptidyl derivatives of ANSA were synthesized according to published protocols.

A random combinatorial approach involves synthesis of a positional scanning library of fluorogenic peptidyl-ANSA to define the substrate specificity or different cancerous cell lines. In contrast to other combinatorial libraries, this library format provides rapid and continuous information on each of the varied substituents in the substrate. A positional scanning library is prepared so that each substrate occupies its own known spot in the array. Specific cleavage of the amide bond after the X residue liberates the fluorescent ANSA, thus allowing for a simple determination of cleavage rates for a library of substrates.

Library synthesis is performed by attaching Fmos-protected ANSA to a solid support through its sulfonyl group. Fmoc solid phase peptide synthesis is performed according to standard protocols in 96-well plates using the FlexChem organic synthesis system of Robbins Scientific. Support-bound peptidyl-ANSA is released in solution, dissolved in DMSO, and transferred to 96-well Microfluor plates for fluorescence analysis. Nineteen natural amino acids (excluding Cys and Met) and unnatural proteinogenic amino acids can be readily incorporated at each of four positions, given more than 13,300 individually localized substrates. The completed library is used for throughput substrate screening for individual proteolytic enzymes, as well as proteolysis by whole cells.

The ANSA derivatives to be used to target proteins according to the present invention are those in which both $R_1$ and $R_2$ are hydrophobic groups, and $R_3$ is preferably a peptidyl group. While not limited to any particular hydrophobic groups, as the type of hydrophobic groups and peptidyl group will depend upon the particular protein targeted, the hydrophobic groups are preferably selected from groups having from about 4 to about 30 carbon atoms. Among the hydrophobic groups that can be used are hydrocarbon groups of 10-16 carbon atoms, which can be branched, cyclic, or linear, with varying degrees of saturation and substitution, carbobenzoxyl, dansyl, vinyl, phenyl, tolyl, and the like, substituted with substituents such as epoxy, mercapto, polyamino, and alkoxycarbonyl.

Preferably, the ANSA derivatives have the following formulae:

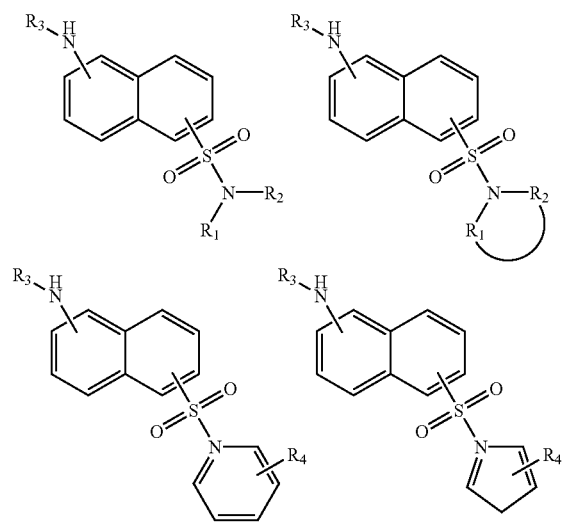

-continued

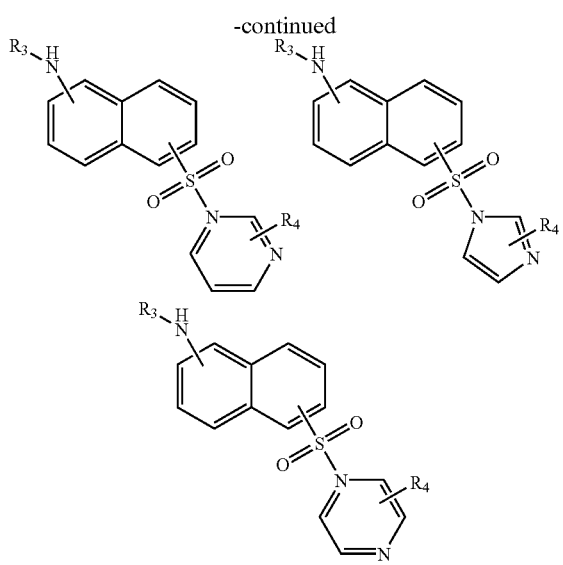

wherein $R_1$, $R_2$ and $R_4$ are hydrogen, $C_1C_{30}$ alkyl, alkyl halide, alkenyl, alkenyl halide, aryl, arylalkyl, and aryl and arylalkyl halides or an affinity group and at least one of $R_1$, $R_2$ and $R_4$ is a hydrophobic group; and $R_3$ is a peptide group.

The ANSA derivatives of the present invention can be used to target pathogenic bacteria. As multiple antibiotic-resistant strains of pathogenic Gram-positive and Gram-negative bacteria have emerged, public health has been seriously threatened because of lack of means to control these bacteria. For example, the ANSA derivatives of the present invention can be designed to target bacteria that cause wound and bloodstream infections, such as vancomycin-resistant *Staphylococcus aureus* or sepsis and meningitis caused by multiple antibiotic-resistant *Streptococcus pneumoniae* strains. These infections are much more common and threatening for hospitalized and/or otherwise exhausted individuals in which standard host defense mechanisms are compromised. Thus, the ANSA derivatives of the present invention can be used as a new class of bactericidal drugs.

The three groups ($R_1$, $R_2$ and $R_3$) chemically attached to ANSA can create virtually an unlimited diversity, and thus these compounds can be made highly specific for their targets. This specificity can be used for recognition and inactivation of only particular types of proteins (e.g., regulatory transcription factors or receptors) as well as for whole cells, such as bacterial cells or cancer cells.

Because the ANSA derivatives are not effective until they are transported to the target cells and enzymatically converted to ANSA in the hydrophobic portion of a cell, they are relatively harmless to cells that are not targeted. The permeability and cleavage of the ANSA derivatives are determined by the structure of the peptide and the ANSA.

ANSA derivatives according to the present invention can be administered by any convenient route, including parenteral, subcutaneous, intravenous, intramuscular, intra peritoneal, or transdermal. Alternatively or concomitantly, administration may be by the oral route. The dosage administered depends upon the age, health, and weight of the recipient, nature of concurrent treatment, if any, and the nature of the effect desired.

Compositions within the scope of the present invention include all compositions wherein the active ingredient is contained in an amount effective to achieve its intended purpose, notably, inhibition of infection or cancer cells. While individual needs vary, determination of optimal ranges of effect amounts of the ANSA derivatives is within the skill of the art. Typical dosages comprise from about 10 nanograms/kg to about 100 mg/kg of body weight.

Pharmaceutical compositions for administering the ANSA derivatives of the present invention preferably contain, in addition to the ANSA derivative, suitable pharmaceutically acceptable carriers comprising excipients and auxiliaries which facilitate processing of the active compounds into preparations which can be used pharmaceutically. Preferably, the preparations, particularly those preparations which are administered orally, and which can be used for the preferred type of administration, such as tablets, dragees, and capsules, as well as suitable suspensions for administration by injection or orally, containing from about 0.0001 to about 99 percent by weight of active compound, together with the excipient. For purposes of the present invention, all percentages are by weight unless otherwise indicated. In addition to the pharmaceutical compositions described here, the compounds of the present invention can be formulated as inclusion complexes, such as cyclodextrin inclusion complexes.

The pharmaceutically acceptable carriers include vehicles, adjuvants, excipients, or dilutes that are well known to those skilled in the art and which are readily available. It is preferred that the pharmaceutically acceptable carrier be one which is chemically inert to the active compounds and which has no detrimental side effects or toxicity under the conditions of use.

The choice of carrier is determined partly by the particular ANSA derivative, as well as by the particular method used to administer the composition. Accordingly, there are a wide variety of suitable formulations of the pharmaceutical compositions of the present invention. Formulation can be prepared for oral, aerosol parenteral, subcutaneous, intravenous intraarterial, intramuscular, intraperitoneal, intratracheal, rectal, and vaginal administration.

Suitable excipients are, in particular, filers, such as saccharides (lactose, sucrose, mannitol, sorbitol), cellulose preparations, and calcium phosphates, such as tricalcium phosphate or calcium hydrogen phosphate. Binders include starch paste using maize starch, wheat starch, rice starch, potato starch, or the like, gelatin, tragacanth, methyl cellulose, hydroxypropylmethylcellulose, and/or polyvinylpyrrolidone.

Other pharmaceutical carriers include liposomes. Since the ANSA derivatives are hydrophobic, the active ingredient is present in the lipidic layer. The lipidic layer generally, but not exclusively, comprises phospholipids such as lecithin and sphingomyelin, steroids such as cholesterol, more or less ionic surfactants such as dicetyl phosphate, stearylamine, or phosphatidic acid.

The compounds may be formulated for transdermal administration, such as in the form of transdermal patches, so as to achieve systemic administration.

Parenteral formulations can be prepared using oils such as petroleum, animal, vegetable, or synthetic oils. Alternative carriers are fatty acids, such as oleic acid, steric acid and isostearic acid.

In determining dosages of the ANSA to be determined, the dosage and frequency of administration is selected in relation to the pharmacological properties of the specific active ingredients. In toxicity studies in general, the highest dose should reach a toxic level but be sublethal for most animals in the group. The lowest dose should induce a biologically demonstrable effect.

The amount of ANSA derivatives to be administered to any given patient must be determined empirically, and will differ depending upon the condition of the patient. Relatively small amounts of the active ingredient can be administered at first, with steadily increasing dosages if no adverse effects are noted. Of course, the maximum safe toxicity dosage as determined in routine animal toxicity test should never be exceeded.

The foregoing description of the specific embodiments will so fully reveal the general nature of the invention that others can, by applying current knowledge, readily modify and/or adapt for various applications such specific embodiments without undue experimentation and without departing from the generic concept. Therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying our various disclosed functions make take a variety of alternative forms without departing from the invention. Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above; and it is intended that such expressions be given their broadest interpretation.

REFERENCES

Al-Mufti et al, "Increase nitric oxide activity in a rat model of acute pancreatitis", *Gut* 43:564-570 (1998)

Ambs et al, "Frequent nitric oxide synthase-2 expression in human colon adenomas: implication for tumor angiogenesis and colon cancer progression", *Cancer Res* 58:334-341 (1998)

Brovkovych et al, "Direct electrochemical measurement of nitric oxide in vascular endothelium", *J Pharm Biomed Anal* 19:135-143 (1999)

Cobbs et al, "Expression of nitric oxide synthase in human centra nervous system tumors", *Cancer Res* 55:727-730 (1995)

Espey et al, "Mechanisms of cell death governed by the balance between nitrosative and oxidative stress", *Ann N Y Acad Sci* 899:209-221 (2000)

Goss et al, "Reactions of *NO, *NO2 and peroxynitrite in membranes: physiological implications", *Free Radic Res* 31(6):597-606 (1999)

Grisham et al, "Nitric oxide. I. Physiological chemistry of nitric oxide and its metabolites: implications in inflammation", *Am. J. Physiol* 276:315-321 (1999)

Ischiropoulos H. "Biological tyrosine nitration: a pathophysiological function of nitric oxide and reactive oxygen species", *Arch Biochem Biophys* 356:1-11 (1998)

Kerwin et al, "Nitric oxide: a new paradigm for second messengers", *J Med Chem* 38(22):4343-4362 (1995)

Kharitonov et al, "Kinetics of nitrosation of thiols by nitric oxide in the presence of oxygen", *J Biol Chem* 270:28158-28164 (1995)

Klotz et al, "Selective expression of inducible nitric oxide synthase in human prostate carcinoma", *Cancer* 82:1897-1903 (1998)

Liu et al, "Accelerated reaction of nitric oxide with $O_2$ within the hydrophobic interior of biological membranes", *Proc Natl Acad Sci USA* 95:2175-2179 (1998)

Mannick et al, "Inducible nitric oxide synthase, nitrotyrosine, and apoptosis in Helicobacter pylori gastritis: effect of antibiotics and antioxidants", *Cancer Res* 56:3238-3243 (1996)

Moncada et al, "Nitric oxide: physiology, pathophysiology, and pharmacology", *Pharmacol Rev* 43(2):109-142 (1991)

Nathan C, "Inducible nitric oxide synthase: what difference does it make?", *J Clin Invest* 100:2417-2423 (1997)

Nedosapasov et al, "Autocatalytic mechanism of protein nitrosylation", *Proc Natl Acad Sci USA* 97:13543-13548 (2000)

Nudler et al, "Transcription processivity: protein-DNA interactions holding together the elongation complex", *Science* 273(5272):211-217 (1996)

Rafikova et al, "Catalysis of S-nitrosothiols by serum albumin: the mechanism and implications in vascular tone control", *Science* submitted (2001)

Stamler et al, "Oxidative modifications in nitrosative stress", *Nat Struct Biol* 5(4):247-249 (1998)

Thomsen et al, "Nitric oxide synthase activity in human gynecological cancer", *Cancer Res* 54:1352-1354 (1994)

Thomsen et al, "Nitric oxide synthase activity in human breast cancer", *Br J Cancer* 72:41-44 (1995)

Williams D L, "Nitrosating agents: is peroxynitrite a likely candidate?", *Nitric Oxide* 1(6):522-527 (1997)

Wilson et al, "Increase expression of inducible nitric oxide synthase and cyclooxygenase-2 in Barrett's esophagus and associated adenocarcinomas", *Cancer Res* 58:2929-2934 (1998)

Wink et al, "Reaction kinetics for nitrosation of cysteine and glutathione in aerobic nitric oxide solutions at neutral pH. Insights into the fate and physiological effects of intermediates generated in the $NO/O_2$ reaction", *Chem Res Toxicol* 7:519-525 (1994)

Zhang et al, "Crystal structure of Thermus aquaticus core RNA polymerase at 3.3 A resolution", *Cell* 98(6):811-824 (1999)

What is claimed is:

1. An ANSA compound of the formula

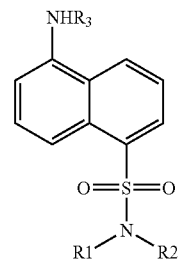

wherein $R_1$ and $R_2$ impart hydrophobicity to the molecule and are selected from the group consisting of $C_{10}$-$C_{16}$ aryl, $C_8$-$C_{30}$ alkyl, $C_8$-$C_{30}$ alkyl halide, $C_{10}$-$C_{16}$ alkenyl, and $C_{10}$-$C_{16}$ alkenyl halide; and $R_3$ is glycyl-glycyl-arginyl-arginyl and at least one of $R_1$ and $R_2$ is a hydrophobic group.

2. L-arginamide glycylglycyl-L-arginyl-N-{(5-[(pentylamino) sulfonyl]-1-naphthenyl}.

3. A pharmaceutical composition for inactivating proteins comprising an effective amount of a compound according to claim 1 and a pharmaceutically acceptable carrier.

* * * * *